United States Patent
Ohba et al.

(10) Patent No.: US 7,153,980 B2
(45) Date of Patent: Dec. 26, 2006

(54) THIOPHENE-CONTAINING COMPOUND AND THIOPHENE-CONTAINING COMPOUND POLYMER

(75) Inventors: Yoshihiro Ohba, Yamagata (JP); Kazuaki Sato, Yamagata (JP); Mieko Seki, Kanagawa (JP); Takeshi Agata, Kanagawa (JP); Katsuhiro Sato, Kanagawa (JP); Kiyokazu Mashimo, Kanagawa (JP); Hirohito Yoneyama, Kanagawa (JP); Hidekazu Hirose, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 432 days.

(21) Appl. No.: 10/783,674

(22) Filed: Feb. 20, 2004

(65) Prior Publication Data

US 2005/0059730 A1    Mar. 17, 2005

(30) Foreign Application Priority Data

Sep. 5, 2003    (JP) .............................. 2003-314140

(51) Int. Cl.
*C07D 333/36*    (2006.01)

(52) U.S. Cl. ...................................................... 549/68
(58) Field of Classification Search .................... 549/68
See application file for complete search history.

(56) References Cited

U.S. PATENT DOCUMENTS

| | | | | |
|---|---|---|---|---|
| 6,396,190 | B1 * | 5/2002 | Ahn et al. ................... | 310/261 |
| 6,840,965 | B1 * | 1/2005 | Chassot et al. ................. | 8/405 |
| 6,841,669 | B1 * | 1/2005 | Cipriani et al. .............. | 544/146 |
| 6,858,223 | B1 * | 2/2005 | Hafner ....................... | 424/434 |
| 6,984,737 | B1 * | 1/2006 | Hartmann et al. ............ | 549/68 |
| 7,015,336 | B1 * | 3/2006 | Reed et al. .................... | 549/59 |
| 7,057,054 | B1 * | 6/2006 | Irie .............................. | 549/59 |

* cited by examiner

*Primary Examiner*—Deborah C. Lambkin
(74) *Attorney, Agent, or Firm*—Fildes & Outland, P.C.

(57) ABSTRACT

The present invention relates to a thiophene-containing compound and a thiophene-containing compound polymer which are useful for organo-electronic devices such as electrophotographic photoreceptors (photosensitive elements), organic electroluminescent elements and organic transistors. More specifically, the invention relates to a thiophene-containing compound and a thiophene-containing compound polymer which are excellent in terms of both charge-transporting properties and luminous properties.

15 Claims, 7 Drawing Sheets

THIOPHENE-CONTAINING COMPOUND AND THIOPHENE-CONTAINING COMPOUND POLYMER

CROSS-REFERENCE TO RELATED APPLICATION

This application claims priority under 35 USC 119 from Japanese Patent Application No. 2003-314140, the disclosure of which is incorporated by reference herein.

BACKGROUND OF THE INVENTION

1. Field of the Invention

The present invention relates to a thiophene-containing compound and a thiophene-containing compound polymer which are useful for organo-electronic devices such as electrophotographic photoreceptors (photosensitive elements), organic electroluminescent elements and organic transistors. More specifically, the invention relates to a thiophene-containing compound and a thiophene-containing compound polymer which are excellent in both charge-transporting properties and luminous properties.

2. Description of the Related Art

Well-known as charge-transporting materials are charge-transporting polymers represented by a polyvinylcarbazole (PVK) and low-molecular dispersion systems obtained by dispersing a charge-transporting low-molecular compound in a polymer. Among these materials, low-molecular dispersion systems are primarily used for electrophotographic photoreceptors because a variety of materials can be used in such systems, and highly functional products can be readily obtained.

Concomitant with the development in recent years of high performance organic photoreceptors, electrophotographic photoreceptors have been used in high speed copying machines and printers. However, at present the performances of these photoreceptors are still not necessarily satisfactory and further developments thereof are highly desirable, specifically in terms of longer-life. By using as a charge-transporting layer comprising the current main stream low-molecular dispersion system, electrophotographic photoreceptors have been obtained which produce satisfactory performances in respect of electrical characteristics. However, such charge-transporting layers have also revealed deficiencies insofar that they use a low-molecular compound dispersed in a polymer and are intrinsically inferior in mechanical strength, thus resulting in poor abrasion resistance.

Organic electroluminescent elements are generally produced by vapor deposition of low-molecular charge-transporting materials. Organic electroluminescent elements have a drawback insofar that a large quantity of Joulean heat caused by a current density as high as several mA/cm$^2$ tends to cause morphologic changes due to, for example, crystallization of such low-molecular charge-transporting materials. Consequently phenomena such as reduction in luminance and dielectric breakdowns have tended to occur, thus curtailing the lifespans of such organic electroluminescent elementals. Only a limited number of materials have both charge-transporting and luminous properties, and organic electroluminescent elements produced therefrom have therefore tended to be unsatisfactory from the standpoints of both efficiency and longevity.

In contrast, for use as a photoconductive material in the production of electrophotographic photoreceptors, the charge-transporting polymer represented by PVK has considerably overcome the above drawbacks, and hence is being intensively studied (see, for example, The 37th Society of Applied Physics & Related Societies of Japan, Preprints, 31p-K-12 (1990)).

Specifically, a polycarbonate obtained by polymerizing a specific dihydroxyarylamine with bischloroformate (see, for example, U.S. Pat. No. 4,806,443) and a polycarbonate obtained by polymerizing a specific dihydroxyarylamine with phosgene (see, for example, U.S. Pat. No. 4,806,444) have been proposed.

Additionally, a polycarbonate obtained by polymerizing a bishydroxyalkylarylamine with bischloroformate or phosgene (see, for example, U.S. Pat. No. 4,801,517), a polycarbonate obtained by polymerizing a specific dihydroxyarylamine, bishydroxyalkylarylamine or bishydroxyalkylamine with bischloroformate, or a polyester obtained by polymerizing one of the above three amines with a bisacyl halide have been disclosed (see, for example, U.S. Pat. Nos. 4,937,165 and 4,959,228).

Moreover, a polycarbonate prepared from an arylamine having a specific fluorene skeleton, a polyester (see, for example, U.S. Pat. No. 5,034,296), and a polyurethane (see, for example, U.S. Pat. No. 4,983,482) have been proposed.

Further, a polyester containing a specific bisstyrylbisarylamine as a main chain (see, for example, Japanese Patent Application Publication (JP-B) No. 59-28903), a polymer having, as a pendant, a charge-transporting substituent such as hydrazone or triarylamine, and photoreceptors produced therefrom (see, for example, Japanese Patent Application Laid-Open (JP-A) Nos. 61-20953, 1-134456, 1-134457, 1-134462, 4-133065 and 4-133066) have been proposed.

On the other hand, an organic electroluminescent element produced from a π conjugate polymer represented by paraphenylenevinylene (PPV) (see, for example, Nature, Vol. 357, 477 (1992)) and an organic electroluminescent element produced from a polymer in which triphenylamine has been introduced into the side chain of a polyphosphazene (see, for example, The 42th Polymer Meeting, Preprints 20J21 (1993)) have been proposed.

Depending on the application, these charge-transporting materials (charge-transporting polymers) are required to have various characteristics such as solubility, film-forming ability, mobility, heat resistance and matching in respect of oxidation potential. In order to satisfy these requirements, an introduction of a substituent is usually conducted, and the properties of the materials are thereby controlled.

Moreover, the physical properties of a charge-transporting polymer have a correlation with the physical properties of a charge-transporting monomer used as the raw material. Therefore, the method of designing the molecular structure of the charge-transporting monomer, namely, a low-molecular material, becomes critical.

For instance, monomers used as the raw material for the above-described triarylamine polymer can be roughly classified into two types, namely, (1) dihydroxyarylamine and (2) bishydroxyalkylarylamine. However, since dihydroxyarylamine has an aminophenol structure, it is susceptible to oxidation and is accordingly difficult to purify. In particular, when it has a parahydroxy-substituted structure, dihydroxyarylamine becomes even more unstable. Furthermore, because it has a structure in which an aromatic ring is directly substituted with oxygen, dihydroxyarylamine has posed problems of generating a biased charge distribution, attributable to electron attractivity caused by oxygen, thus leading to reduced mobility. On the other hand, bishydroxyalkylarylamine does not have such a problem with regard to electron attractivity, since owing to the presence of a methylene group, bishydroxyalkylarylamine is not affected by oxygen. Nonetheless, synthesis of bishydroxyalkylarylamine has proved difficult. In more detail, when diarylamine or diarylbenzidine is allowed to react with 3-bromoiodobenzene, the resultant product tends to be a mixture of product materials, because bromine and iodine, present in 3-bromoiodobenzene, are both highly reactive, and therefore a reduced yield is produced. Also, another problem has been that alkyl lithium and ethylene oxide, employed when bromine is made into a lithium product, are dangerous and highly toxic, and thus require the greatest care in handling.

Moreover, the aforementioned organic electroluminescent elements produced from the π conjugate polymer represented by paraphenylenevinylene (PPV), or from the polymer in which triphenylamine has been introduced into the side chain of a polyphosphazene, have deficiencies in terms of properties of tone, luminous intensity, durability and the like.

Therefore, in order to develop organic electronic devices such as organic electroluminescent elements which exhibit higher luminous intensity and good stability even when they are used repeatedly, it is desirable to develop organic electronic materials which can be readily synthesized, and which also have both high charge-transporting properties and excellent luminous properties.

SUMMARY OF THE INVENTION

The inventors accomplished the present invention by conducting extensive research in view of the aforementioned drawbacks and discovering that a thiophene-containing compound represented by the following formula (I) and a thiophene-containing compound polymer represented by either of the following formulae (V-1) and (V-2) can be readily produced, and exhibit good charge-transporting ability, luminous properties and film-forming ability.

According to a first aspect of the invention, a thiophene-containing compound is provided represented by the following formula (I):

Formula (1)

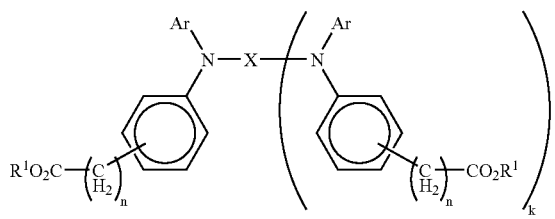

wherein, in formula (I), Ar represents one or more thiophene rings, a monovalent aromatic group containing one or more thiophene rings or a monovalent aromatic group; X represents one or more thiophene rings, a monovalent or divalent aromatic group containing one or more thiophene rings or a monovalent or divalent aromatic group, in which all of the thiophene rings and aromatic groups may be unsubstituted or further may have a substituent; $R^1$ represents a hydrogen atom, an alkyl group, a substituted or unsubstituted aryl group or a substituted or unsubstituted aralkyl group; n indicates an integer of from 0 to 5; and k indicates 0 or 1; provided that at least one of Ar and X contains a thiophene ring.

According to a second aspect of the invention, a thiophene-containing compound polymer is provided represented by the following formula (V-1) or (V-2):

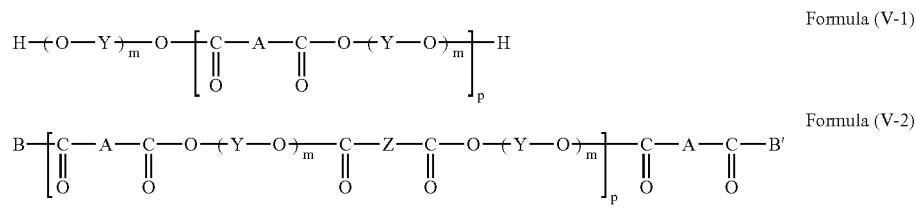

Formula (V-1)

Formula (V-2)

wherein, in formulae (V-1) and (V-2), Y represents a divalent hydrocarbon group; Z represents a divalent hydrocarbon group; B and B' each independently represent —O—$(Y—O)_m$—H or —O—$(Y—O)_m$—CO-Z-CO—OR , in which $R^2$ represents a hydrogen atom, an alkyl group, a substituted or unsubstituted aryl group or a substituted or unsubstituted aralkyl group; m indicates an integer of from 1 to 5, and p indicates an integer of from 5 to 5,000; and A represents a group represented by the following formula (VI):

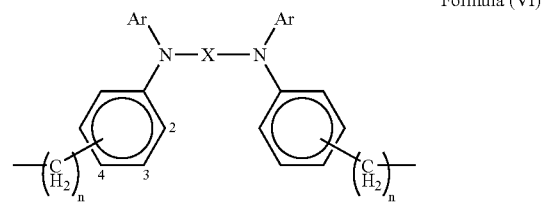

Formula (VI)

wherein, in formula (VI), Ar represents one or more thiophene rings, a monovalent aromatic group containing one or more thiophene rings or a substituted or unsubstituted monovalent aromatic group; X represents one or more thiophene rings, a divalent aromatic group containing one or more thiophene rings or a divalent aromatic group, in which all of the thiophene rings and aromatic groups may be unsubstituted or further may have a substituent; and n indicates an integer of from 0 to 5; provided that at least one of Ar and X contains a thiophene ring.

DETAILED DESCRIPTION OF THE INVENTION

Figure 1:
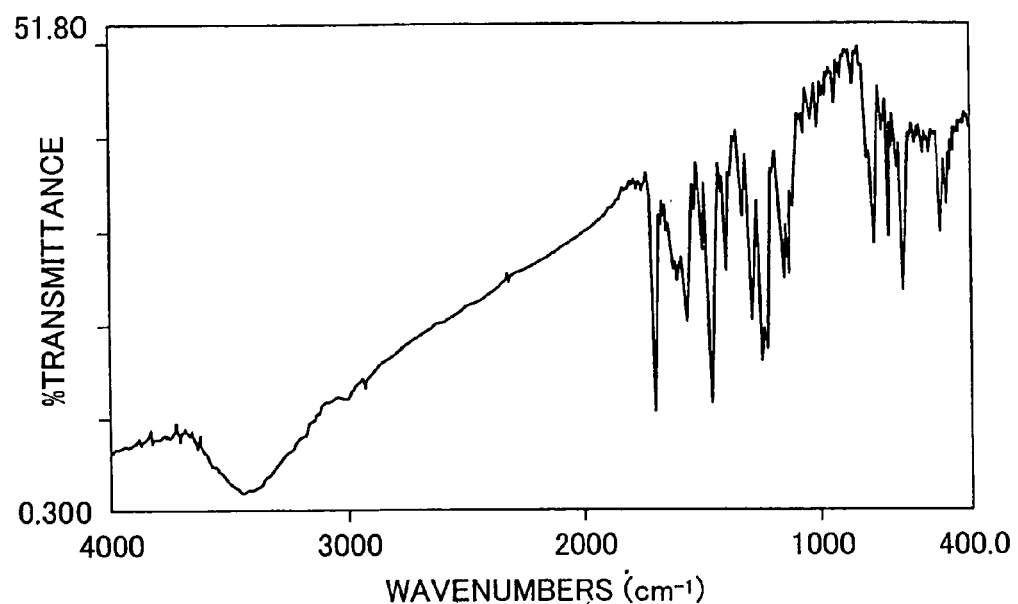
FIG. 1 is an IR spectrum of a thiophene-containing compound (Exemplary Compound 2) obtained in Example 1.

Hereinafter, a thiophene-containing compound of the present invention will be explained in detail.

The thiophene-containing compound of the invention is a thiophene-containing compound represented by the following formula (I).

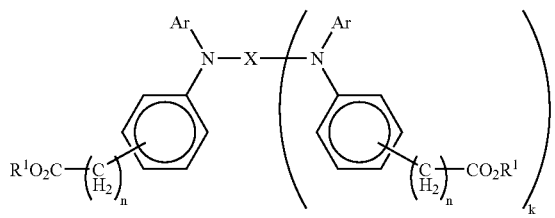

Formula (I)

In the formula (I), Ar represents one or more thiophene rings, a monovalent aromatic group containing one or more thiophene rings or a monovalent aromatic group; X represents one or more thiophene rings, a monovalent or divalent aromatic group containing one or more thiophene rings or a monovalent or divalent aromatic group, in which all the aforementioned thiophene rings and aromatic groups may be unsubstituted or further may have a substituent. $R^1$ represents a hydrogen atom, an alkyl group, a substituted or unsubstituted aryl group, or a substituted or unsubstituted aralkyl group. n indicates an integer of from 0 to 5. k indicates 0 or 1. In the formula, at least one of Ar and X contains a thiophene ring. When the above k indicates 1, two of Ar, two of $R^1$ and two of n are respectively present in the formula. In this case, the two of Ar and the two of $R^1$ may respectively represent different groups, and the two of n may indicate different integers.

The thiophene-containing compound according to the invention can exhibit enhanced luminous properties and high mobility, due to the facts that it contains one or more thiophene rings.

Ar in the above formula (I) represents one or more thiophene rings, a monovalent aromatic group containing one or more thiophene rings or a monovalent aromatic group, in which all the aforementioned thiophene rings and aromatic groups may be unsubstituted or further may have a substituent.

Examples of the above one or more thiophene rings represented by Ar include a thienyl group, bithienyl group and terthienyl group. As the monovalent aromatic group represented by Ar, monovalent aromatic groups having 1 to 10 aromatic rings are preferable. Also, examples of the monovalent aromatic group containing a thiophene ring represented by Ar include monovalent aromatic groups having a condensed or polynuclear ring, such as phenyl groups, biphenyl groups, terphenyl groups, naphthyl groups, phenanthrenyl groups, anthracenyl groups, pyrenyl groups, fluorenyl groups and styryl groups, which are substituted with a thiophene ring.

Examples of the substituent with which the monovalent aromatic group represented by Ar is further substituted include a hydrogen atom, an alkyl group, an alkoxy group, an aryl group, an aralkyl group, a substituted amino group and a halogen atom.

As the alkyl group with which the monovalent aromatic group is further substituted, alkyl groups having 1 to 10 carbon atoms are preferable, and examples of these alkyl groups include a methyl group, an ethyl group, a propyl group and an isopropyl group.

As the alkoxy group with which the monovalent aromatic group is further substituted, alkoxy groups having 1 to 10 carbon atoms are preferable, and examples of these alkoxy groups include a methoxy group, an ethoxy group, a propoxy group and an isopropoxy group.

As the aryl group with which the monovalent aromatic group is further substituted, aryl groups having 6 to 20 carbon atoms are preferable, and examples of these aryl groups include a phenyl group and a tolyl group.

As the aralkyl group with which the monovalent aromatic group is further substituted, aralkyl groups having 7 to 20 carbon atoms are preferable, and examples of these aralkyl groups include a benzyl group and a phenethyl group.

Examples of the substituent in the substituted amino group with which the monovalent aromatic group is further substituted include an alkyl group, an aryl group and an aralkyl group.

As the halogen atom with which the monovalent aromatic group is further substituted, a chlorine atom is preferable.

Examples of the substituent with which the above thiophene ring is further substituted include an alkyl group, an alkoxy group, an aryl group, an aralkyl group and a halogen atom.

$R^1$ in formula (I) represents a hydrogen atom, an alkyl group, a substituted or unsubstituted aryl group, or a substituted or unsubstituted aralkyl group.

As the alkyl group represented by $R^1$, those having 1 to 4 carbon atoms are preferable, and examples of the alkyl group include a methyl group, an ethyl group, a propyl group and an isopropyl group.

As the substituted or unsubstituted aryl group represented by $R^1$, those having 6 to 20 carbon atoms are preferable, and examples of the aryl group include a phenyl group and a tolyl group.

As the substituted or unsubstituted aralkyl group represented by $R^1$, those having 7 to 20 carbon atoms are preferable, and examples of the aralkyl group include a benzyl group and a phenethyl group.

X in formula (I) represents one or more thiophene rings, a monovalent or divalent aromatic group having one or more thiophene rings or a monovalent or divalent aromatic group. The aromatic group represented by X is monovalent when k is 0, or it is divalent when k is 1.

X is preferably a group represented by any one selected from the group consisting of the following formulae (II-1) to (II-4).

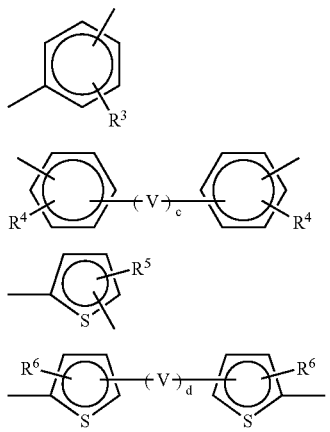

Formula (II-1)

Formula (II-2)

Formula (II-3)

Formula (II-4)

In the above formulae (II-1) to (II-4), $R^3$, $R^4$, $R^5$ and $R^6$ each independently represent a hydrogen atom, an alkyl group, an alkoxy group, a substituted or unsubstituted aryl group, a substituted or unsubstituted aralkyl group or a halogen atom. c and d each indicate an integer of from 0 to 5. V represents a group represented by any one selected from the group consisting of the following formulae (III-1) to (III-11). In the following formulae (III-1) to (III-11). In the following formulae (III)-1) to (III-11), e indicates an interger of from 1 to 5; and f and g each indicate an integer of from 0 to 5.

—(CH$_2$)$_e$—    Formula (III-1)

—C(CH$_3$)$_2$—    Formula (III-2)

—O—    Formula (III-3)

—S—    Formula (III-4)

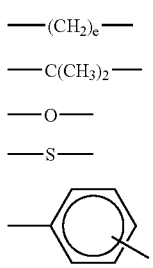

Formula (III-5)

-continued

Formula (III-6)

—C(CF$_3$)$_2$—    Formula (III-7)

—Si(CH$_3$)$_2$—    Formula (III-8)

—CH═CH—    Formula (III-9)

Formula (III-10)

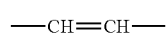

Formula (III-11)

As the alkyl group represented by $R^3$, $R^4$, $R^5$ and $R^6$, alkyl groups having 1 to 4 carbon atoms are preferable, and examples of the alkyl group include a methyl group, an ethyl group, a propyl group and an isopropyl group.

As the alkoxy group represented by $R^3$, $R^4$, $R^5$ and $R^6$, alkoxy groups having 1 to 4 carbon atoms are preferable, and examples of the alkoxy group include a methoxy group, an ethoxy group, a propoxy group and an isopropoxy group.

As the substituted or unsubstituted aryl group represented by $R^3$, $R^4$, $R^5$ and $R^6$, those having 7 to 20 carbon atoms are preferable, and examples of the aryl group include a phenyl group and a tolyl group.

As the substituted or unsubstituted aralkyl group represented by $R^3$, $R^4$, $R^5$ and $R^6$, those having 7 to 20 carbon atoms are preferable, and examples of the aralkyl group include a benzyl group and a phenethyl group.

Examples of the halogen atom represented by $R^3$, $R^4$, $R^5$ and $R^6$ include a chlorine atom and a bromine atom.

X is preferably a group represented by any one selected from the group consisting of the following formulae (IV-1) to (IV-4). In the following formulae (IV-1) to (IV-4), a indicates an integer of from 0 to 10; and b indicates an integer of from 1 to 10.

Formula (IV-1)

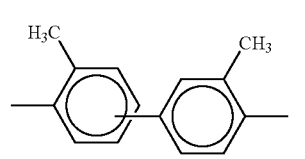

Formula (IV-2)

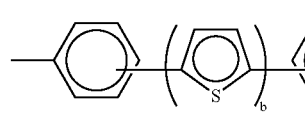

Formula (IV-3)

-continued

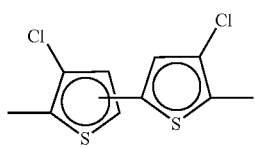

Formula (IV-4)

Specific examples (Exemplary Compounds 1 to 57) of the thiophene-containing compound represented by formula (I) according to the invention are shown below: however, these examples are not intended to be limiting of the invention. In the following Tables 1 to 4, the bonding position indicates a position at which $R^1O_2C-(CH_2)_n-$ is bound (meaning that, in the formula shown above each table, $R^1O_2C-(CH_2)_n-$ is bound at one of the positions on the benzene ring having one of numbers from 2 to 4 or from 2' to 4'). Also, when k in the table indicates 1, two of Ar, two of $R^1$ and two of n are each present, and each of these three pairs respectively represents a group or an integer as shown in the table.

TABLE 1

| Compound No. | X | Ar | Bonding Position | k | n | $R^1$ |
|---|---|---|---|---|---|---|
| 1 | phenyl | thienyl-phenyl | 3 | 0 | 2 | —CH₃ |
| 2 | phenyl | thienyl-phenyl | 4 | 0 | 2 | —CH₃ |
| 3 | phenyl | bithienyl-phenyl | 4 | 0 | 2 | —CH₃ |
| 4 | biphenyl | thienyl-phenyl | 4 | 0 | 2 | —CH₃ |
| 5 | biphenyl | bithienyl-phenyl | 4 | 0 | 2 | —CH₃ |
| 6 | terphenyl | thienyl-phenyl | 4 | 0 | 2 | —CH₃ |
| 7 | biphenyl | thienyl-phenyl | 4,4' | 1 | 2 | —CH₃ |
| 8 | biphenyl | bithienyl-phenyl | 4,4' | 1 | 2 | —CH₃ |
| 9 | biphenyl | thienyl | 3,3' | 1 | 2 | —CH₃ |

TABLE 1-continued $$\text{R}^1\text{O}_2\text{C}\left(\underset{\text{H}_2}{\text{C}}\right)_n \underset{3}{\overset{2}{\bigcirc}} \underset{\text{Ar}}{\overset{}{\text{N}}} - \text{X} \left( \underset{\text{Ar}}{\overset{}{\text{N}}} \underset{3'}{\overset{2'}{\bigcirc}} \left(\underset{\text{H}_2}{\text{C}}\right)_n \text{CO}_2\text{R}^1 \right)_k$$

| Compound No. | X | Ar | Bonding Position | k | n | $R^1$ |
|---|---|---|---|---|---|---|
| 10 | biphenyl | bithiophene | 4,4' | 1 | 2 | —CH$_3$ |
| 11 | biphenyl | terthiophene | 4,4' | 1 | 2 | —CH$_3$ |
| 12 | biphenyl | phenyl-thiophene-phenyl | 4,4' | 1 | 2 | —CH$_3$ |
| 13 | biphenyl | thiophene-phenyl-thiophene-phenyl | 4,4' | 1 | 2 | —CH$_3$ |
| 14 | biphenyl | phenyl-thiophene-phenyl-thiophene-phenyl | 3,3' | 1 | 2 | —CH$_3$ |
| 15 | biphenyl | phenyl-bithiophene-phenyl | 4,4' | 1 | 2 | —CH$_3$ |
| 16 | biphenyl | phenyl-terthiophene-phenyl | 4,4' | 1 | 2 | —CH$_3$ |
| 17 | biphenyl | phenyl-thiophene | 4,4' | 1 | 3 | —CH$_3$ |

TABLE 2

$$\text{R}^1\text{O}_2\text{C}\left(\underset{\text{H}_2}{\text{C}}\right)_n \underset{3}{\overset{2}{\bigcirc}} \underset{\text{Ar}}{\overset{}{\text{N}}} - \text{X} \left( \underset{\text{Ar}}{\overset{}{\text{N}}} \underset{3'}{\overset{2'}{\bigcirc}} \left(\underset{\text{H}_2}{\text{C}}\right)_n \text{CO}_2\text{R}^1 \right)_k$$

| Compound No. | X | Ar | Bonding Position | k | n | $R^1$ |
|---|---|---|---|---|---|---|
| 18 | biphenyl | phenyl-bithiophene | 4,4' | 1 | 2 | —CH$_3$ |

TABLE 2-continued

| Compound No. | X | Ar | Bonding Position | k | n | R[1] |
|---|---|---|---|---|---|---|
| 19 | 3,3'-dimethylbiphenyl-4,4'-diyl | thiophene-phenylene | 4,4' | 1 | 2 | —CH$_3$ |
| 20 | 3,3'-dimethylbiphenyl-4,4'-diyl | bithiophene-phenylene | 4,4' | 1 | 2 | —CH$_3$ |
| 21 | 3,3'-dimethylbiphenyl-4,4'-diyl | thiophene | 4,4' | 1 | 1 | —CH$_3$ |
| 22 | 3,3'-dimethylbiphenyl-4,4'-diyl | bithiophene | 3,3' | 1 | 3 | —CH$_3$ |
| 23 | 3,3'-dimethylbiphenyl-4,4'-diyl | terthiophene | 4,4' | 1 | 2 | —CH$_3$ |
| 24 | 3,3'-dimethylbiphenyl-4,4'-diyl | phenyl-thiophene-phenylene | 3,3' | 1 | 2 | —CH$_3$ |
| 25 | 3,3'-dimethylbiphenyl-4,4'-diyl | thiophene-phenylene-thiophene-phenylene | 4,4' | 1 | 2 | —CH$_3$ |
| 26 | 3,3'-dimethylbiphenyl-4,4'-diyl | phenyl-thiophene-phenylene-thiophene-phenylene | 4,4' | 1 | 3 | —CH$_3$ |
| 27 | 3,3'-dimethylbiphenyl-4,4'-diyl | phenyl-thiophene-thiophene-phenylene | 4,4' | 1 | 2 | —CH$_3$ |

TABLE 2-continued

| Compound No. | X | Ar | Bonding Position | k | n | R¹ |
|---|---|---|---|---|---|---|
| 28 | 3,3'-dimethylbiphenyl-4,4'-diyl | phenyl-terthiophene-phenyl | 3,3' | 1 | 3 | —CH₃ |
| 29 | 3,3'-dimethylbiphenyl-4,4'-diyl | phenyl-thiophene | 3,3' | 1 | 2 | —CH₃ |
| 30 | 3,3'-dimethylbiphenyl-4,4'-diyl | phenyl-bithiophene | 4,4' | 1 | 2 | —CH₃ |
| 31 | p-terphenyl-4,4''-diyl | thiophene-phenyl | 4,4' | 1 | 2 | —CH₃ |
| 32 | p-terphenyl-4,4''-diyl | bithiophene-phenyl | 4,4' | 1 | 2 | —CH₃ |

TABLE 3

| Compound No. | X | Ar | Bonding Position | k | n | R¹ |
|---|---|---|---|---|---|---|
| 33 | p-terphenyl-4,4''-diyl | 4-chlorothiophene | 4,4' | 1 | 2 | —CH₃ |
| 34 | p-terphenyl-4,4''-diyl | bithiophene | 4,4' | 1 | 2 | —CH₃ |

TABLE 3-continued

| Compound No. | X | Ar | Bonding Position | k | n | R¹ |
|---|---|---|---|---|---|---|
| 35 | terphenyl | terthiophene | 4,4' | 1 | 2 | —CH₃ |
| 36 | terphenyl | phenyl-thiophene-phenyl | 4,4' | 1 | 2 | —CH₃ |
| 37 | terphenyl | thiophene-phenyl-thiophene-phenyl | 4,4' | 1 | 2 | —CH₂CH₃ |
| 38 | terphenyl | phenyl-thiophene-phenyl-thiophene-phenyl | 4,4' | 1 | 3 | —CH₃ |
| 39 | terphenyl | phenyl-bithiophene-phenyl | 4,4' | 1 | 3 | —CH₃ |
| 40 | terphenyl | phenyl-terthiophene-phenyl | 3,3' | 1 | 2 | —CH₃ |
| 41 | terphenyl | phenyl-thiophene | 3,3' | 1 | 2 | —CH₃ |
| 42 | terphenyl | phenyl-bithiophene | 4,4' | 1 | 2 | —CH₂CH₃ |
| 43 | dichloro-bithiophene | phenyl | 4,4' | 1 | 2 | —CH₃ |
| 44 | dichloro-bithiophene | biphenyl | 4,4' | 1 | 2 | —CH₃ |
| 45 | dichloro-bithiophene | thiophene-phenyl | 4,4' | 1 | 2 | —CH₃ |

TABLE 3-continued

| Compound No. | X | Ar | Bonding Position | k | n | R¹ |
|---|---|---|---|---|---|---|
| 46 | (dichloro-bithiophene) | (thiophene-thiophene-phenyl) | 4,4' | 1 | 2 | —CH₃ |
| 47 | (phenyl-bithiophene-phenyl) | (phenyl) | 4,4' | 1 | 2 | —CH₃ |
| 48 | (phenyl-bithiophene-phenyl) | (thiophene-phenyl) | 4,4' | 1 | 2 | —CH₃ |

TABLE 4

| Compound No. | X | Ar | Bonding Position | k | n | R¹ |
|---|---|---|---|---|---|---|
| 49 | (phenyl-bithiophene-phenyl) | (thiophene-thiophene-phenyl) | 4,4' | 1 | 2 | —CH₃ |
| 50 | (phenyl-(bithiophene)₂-phenyl) | (phenyl) | 4,4' | 1 | 2 | —CH₃ |
| 51 | (phenyl-(bithiophene)₂-phenyl) | (biphenyl) | 4,4' | 1 | 2 | —CH₃ |
| 52 | (phenyl-(bithiophene)₂-phenyl) | (thiophene-phenyl) | 4,4' | 1 | 2 | —CH₃ |
| 53 | (phenyl-(bithiophene)₂-phenyl) | (thiophene-thiophene-phenyl) | 4,4' | 1 | 2 | —CH₂CH₃ |
| 54 | (bithiophene) | (phenyl) | 4,4' | 1 | 2 | —CH(CH₃)₂ |

TABLE 4-continued

| Compound No. | X | Ar | Bonding Position | k | n | R¹ |
|---|---|---|---|---|---|---|
| 55 | bithiophene | biphenyl | 4,4' | 1 | 2 | —CH₃ |
| 56 | terthiophene | phenyl | 4,4' | 1 | 2 | —CH₃ |
| 57 | terthiophene | biphenyl | 4,4' | 1 | 2 | —CH₂CH₃ |

Hereinafter, synthesis of the thiophene-containing compound of the invention will be explained.

As examples of the methods of synthesizing the thiophene-containing compound of the invention, the following methods (1) and (2) are given.

(1) Arylamine is reacted with carboalkoxyalkylbenzene halide or carboalkoxybenzene halide to synthesize a diarylamine, and then the obtained diarylamine is reacted with benzidine bishalide.

(2) Arylamine, diarylbenzidine or the like is reacted with carboalkoxyalkylbenzene halide or carboalkoxybenzene halide.

As to the synthesis of a charge-transporting material having an alkylene carboxylate group, a method in which after a chloromethyl group has been introduced and a Grignard's reagent has been formed using Mg and then converted into a carboxylic acid using carbon dioxide, esterification is carried out is described in JP-A No. 5-80550.

However, in this method, the chloromethyl group cannot be introduced during the initial stage using the raw material, because the chloromethyl group is highly reactive. Therefore, it is necessary that the methyl group introduced during the initial stage by using the raw material is chloromethylated after a skeleton such as a triarylamine or tetraarylbenzidine is formed; or an unsubstituted one is employed during the initial stage using the raw material, a tetraarylbenzene skeleton is formed and then a functional group such as a formyl group is introduced by causing a substitution reaction into an aromatic ring, followed by a reducing reaction to form an alcohol, which is then introduced to a chloromethyl group by using a halogenating reagent such as thionyl chloride, or alternatively is directly subjected to chloromethylation using paraformaldehyde, hydrochloric acid and the like.

However, because a charge-transporting material having a skeleton such as triarylamine or tetraarylbenzidine is highly reactive, a substitution reaction of a halogen on an aromatic ring easily takes place in the method of chloromethylating the introduced methyl group, and it is therefore substantially impossible to chlorinate only a methyl group selectively. Also, in the method in which an unsubstituted one is used during the initial stage using the raw material to be introduced to a chloromethyl group after a functional group such as a formyl group has been introduced or in the method of direct chloromethylation, the chloromethyl group is only introduced at a para position relative to a nitrogen atom, and therefore, an alkylene carboxylate group is introduced only at a para position relative to the nitrogen atom. Furthermore, the method of introducing a chloromethyl group after having introduced a formyl group requires a longsome reaction step.

In contrast, the method in which arylamine, diarylbenzidine or the like is reacted with a carboalkoxyalkylbenzene halide to obtain a monomer is advantageous in such a point that it is easy to change the position of a substituent and to control an ionizing potential. Specifically, this method makes it possible to control the ionizing potential of the compound. The aforementioned diamine compound permits various substituents to be introduced at arbitrary positions and further is chemically stable and can be handled easily, whereby the aforementioned problems are overcome.

An illustrative method of synthesizing the thiophene-containing compound of the invention will be explained below. In this illustrative method of synthesizing the thiophene-containing compound, firstly diarylamine of the following formula (XIII) is synthesized. Examples of the method of synthesizing diarylamine include a method in which a compound of the following formula (IX) and a compound of the following formula (X) are subjected to a coupling reaction using a copper catalyst, and a method in which a compound of the following formula (XI) and a compound of the following formula (XII) are subjected to a coupling reaction using a copper catalyst.

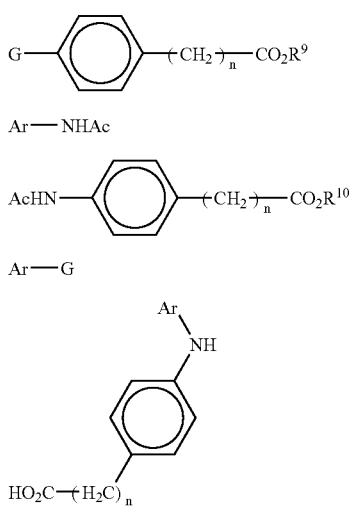

Formula (IX)

Formula (X)

Formula (XI)

Formula (XII)

Formula (XIII)

In the above formula (IX), $R^9$ represents a hydrogen atom, an alkyl group, a substituted or unsubstituted aryl group or a substituted or unsubstituted aralkyl group; G represents a bromine atom or an iodine atom; and n indicates an integer of from 0 to 5.

Ar in the formula (X) is the same as Ar defined in the above formula (I); and Ac represents an acetyl group.

In the above formula (XI), $R^{10}$ represents a hydrogen atom, an alkyl group, a substituted or unsubstituted aryl group or a substituted or unsubstituted aralkyl group; n indicates an integer of from 0 to 5; and Ac represents an acetyl group.

Ar in the above formula (XII) is the same as defined in formula (I); and G is the same as defined in formula (IX).

Ar in the above formula (XIII) is the same as defined in formula (I); and n indicates an integer of from 0 to 5.

The obtained diarylamine of formula (XIII) is subjected to a coupling reaction together with a compound of the following formula (XIV) in the presence of a copper catalyst, and consequently, the thiophene-containing compound of the invention can be synthesized. In the following formula (XIV), X is the same as defined in formula (I); G is the same as defined in formula (IX); and s indicates 0 or 1.

-X(-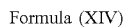)$_s$              Formula (XIV)

First, description will be given of the coupling reaction to synthesize diarylamine of formula (XIII). In this coupling reaction, it is preferable to use the compound of formula (IX) or (XII) in an amount 0.5 to 1.5 equivalents, and preferably 0.7 to 1.2 equivalents, based on 1 equivalent of the compound of formula (X) or (XI).

As the copper catalyst used in the coupling reaction to synthesize diarylamine of formula (XIII), a copper powder, cuprous oxide, copper iodide, copper sulfate or the like may be used. The copper catalyst is used in an amount of preferably 0.001 to 3 parts by mass, and more preferably 0.01 to 2 parts by mass, based on 1 part by mass of the compound of formula (X) or (XI).

It is not always necessary to employ a solvent in the coupling reaction for synthesizing diarylamine of formula (XIII). As a solvent for use in the reaction, a high-boiling water-insoluble hydrocarbon-type solvent such as n-tridecane, tetralin, p-cymene or terpinolene or a high-boiling halogen-type solvent such as o-dichlorobenzene or chlorobenzene may be preferably used. The solvent is used in an amount of preferably 0.1 to 3 pass parts, and more preferably 0.2 to 2 parts by mass, based on 1 part of the compound of formula (X) or (XI). Also, this coupling reaction is allowed to proceed at a temperature ranging from 100 to 300° C., preferably 150 to 270° C., and more preferably 180 to 250° C., with providing sufficient stirring in an atmosphere of inert gas such as nitrogen or argon, and preferably run while removing water generated in the reaction.

After the reaction is complete, it is preferable that after having cooled the reaction solution as necessary, a hydrolysis reaction is effected using a solvent such as methanol, ethanol, n-octanol, ethylene glycol, propylene glycol or glycerine, and a base.

As the base, sodium hydroxide, potassium hydroxide, sodium carbonate or potassium carbonate may be used. The base is used in an amount of 0.5 to 3 equivalents, and preferably 0.7 to 2 equivalents, based on 1 equivalent of the compound of formula (X) or (XI).

The amount of the solvent used in the hydrolysis reaction is 0.5 to 10 parts by mass, and preferably 1 to 5 parts by mass, based on 1 part of the compound of formula (X) or (XI). The amount of the base used is 0.2 to 5 parts by mass, and preferably 0.3 to 3 parts by mass, based on 1 part of the compound of formula (X) or (XI).

The aforementioned hydrolysis reaction is run in the following manner: after the coupling reaction is completed, a solvent and a base are added directly in the reaction solution to cause the reaction at a temperature ranging from 50° C. to the boiling point of the solvent, with providing sufficient stirring in an atmosphere of inert gas such as nitrogen or argon. In this case, it is preferable to use, as the solvent, a high-boiling solvent having a boiling point of 150° C. or higher to permit an elevated reaction temperature, in considering that carboxylate is generated in the coupling reaction and solidified. It is particularly preferable to use, as the solvent, water-soluble ethylene glycol, propylene glycol or glycerine such that diarylamine of formula (XIII) can be released by further neutralization using hydrochloric acid after the reaction solution has been poured into water in the post-treatment. After the hydrolysis reaction is completed, the reaction product is poured into water, followed by further neutralization using hydrochloric acid to thereby release diarylamine of formula (XIII). Then, the obtained product is sufficiently washed and dissolved in a proper solvent, as necessary. Thereafter, the resultant solution is column-purified, for example, by using silica gel, alumina, activated clay or activated carbon or by adding these adsorbents in the solution to adsorb unnecessary substances. Alternatively, the resultant solution is further re-crystallized, for purification, from a proper solvent such as acetone, ethanol, ethyl acetate or toluene, or may be subjected to the same process after esterified into a methyl ester, ethyl ester or the like.

Next, the resulting diarylamine of formula (XIII) and the compound of formula (XIV) are subjected to a coupling reaction using a copper catalyst. Then, the resulting product is esterified into a methyl ester or an ethyl ester. Alternatively, diarylamine of formula (XIII) is esterified into the methyl ester or the ethyl ester, which is then subjected to another coupling reaction with the compound of formula (XIV) in the presence of a copper catalyst, whereby the thiophene-containing compound represented by formula (I) can be obtained.

In the case of using a halogen di-substituted product as the compound of formula (XIV) in the coupling reaction between diarylamine of formula (XIII) and the compound of formula (XIV), the compound of formula (XIV) is used in an an amount of 1.5 to 5 equivalents, and preferably 1.7 to 4 equivalents, based on 1 equivalent of diarylamine of formula (XIII). As the copper catalyst in this case, a copper powder, cuprous oxide, copper iodide or copper sulfate may be used. The copper catalyst is used in an amount of preferably 0.001 to 3 parts by mass, and more preferably 0.01 to 2 parts by mass, based on 1 part by mass of diarylamine represented by formula (XIII). As the base, sodium hydroxide, potassium hydroxide, sodium carbonate or potassium carbonate may be used. The base is used in an amount of preferably 1 to 6 equivalents, and more preferably 1.4 to 4 equivalents, based on 1 equivalent of diarylamine represented by formula (XIII). Preferable examples of the solvent, which is used if necessary, include high-boiling water-insoluble hydrocarbon-type solvents such as n-tridecane, tetralin, p-cymene or terpinolene, or a high-boiling halogen-type solvent such as o-dichlorobenzene or chlorobenzene may be used. The solvent is used in an amount of preferably 0.1 to 3 pass parts, and more preferably 0.2 to 2 parts by mass, based on 1 part by mass of diarylamine of formula (XIII).

Also, this coupling reaction is run at a temperature ranging from 100 to 300° C., preferably 150 to 270° C., and more preferably 180 to 250° C., with providing sufficient stirring in an atmosphere of inert gas such as nitrogen or argon, and preferably run while removing water generated in the reaction. After the reaction is completed, the reaction product is dissolved in a solvent such as toluene, isoper or n-tridecane, and unnecessary substances are removed by washing with water or filtration. Further, the resulting solution is column-purified, for example, by using silica gel, alumina, activated clay or activated carbon or by adding these adsorbents in the solution to adsorb unnecessary substances. For purification, the solution is re-crystallized from a proper solvent such as ethanol, ethyl acetate or toluene.

In the case of using a halogen mono-substituted product as the compound of formula (XIV) in the coupling reaction, the compound of formula (XIV), a copper catalyst, a base, and a solvent as necessary, are used. As the copper catalyst, a copper powder, cuprous oxide, copper iodide, copper sulfate or the like may be used. The copper catalyst is used in an amount of preferably 0.001 to 3 parts by mass, and more preferably 0.01 to 2 parts by mass, based on 1 part by mass of the compound of formula (XIII). As the base, sodium hydroxide, potassium hydroxide, sodium carbonate or potassium carbonate may be used. The base is used in an amount of preferably 0.5 to 3 equivalents, and more preferably 0.7 to 2 equivalents, based on 1 equivalent of diarylamine of formula (XIII). Examples of the solvent include high-boiling water-insoluble hydrocarbon-type solvents such as n-tridecane, tetralin, p-cymene or terpinolene, or a high-boiling halogen-type solvent such as o-dichlorobenzene or chlorobenzene. The solvent is used in an amount of preferably 0.1 to 3 pass parts, and more preferably 0.2 to 2 parts by mass, based on 1 part of diarylamine of formula (XIII). The post-treatment and purification performed after the coupling reaction are carried out, in the same manner as conducted in the case where the compound of formula (XIV) is used as the halogen di-substituted product.

In the case of using the halogen di-substituted product, X is preferably a group represented by any one selected from the group consisting of the following formulae (VIII-1) to (VIII-4) from the standpoints of stability and mobility. In the following formulae (VIII-1) to (VIII-4), b indicates an integer of from 1 to 5.

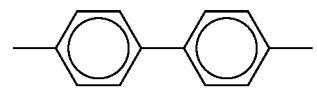

Formula (VIII-1)

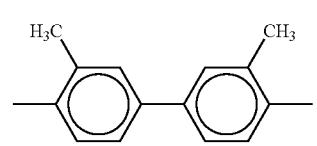

Formula (VIII-2)

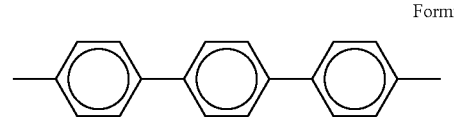

Formula (VIII-3)

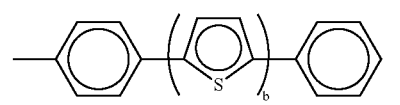

Formula (VIII-4)

The thiophene-containing compound according to the invention may also be synthesized in the following manner: a compound (triarylamine) of the following formula (XV) is synthesized by a coupling reaction using a copper catalyst in the same manner as above, and is converted into a compound of the following formula (XVI) by halogenation using N-bromosuccinic acid imide (NBS), N-chlorosuccinic acid imide (NCS) or the like, and thereafter, the resulting compound is subjected to a homo-coupling reaction using a nickel catalyst.

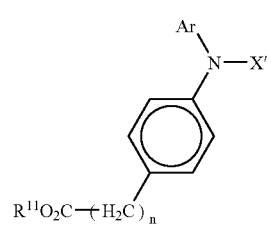

Formula (XV)

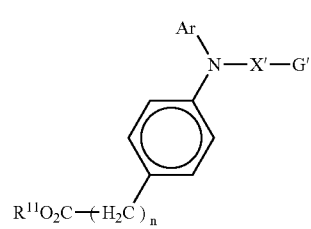

Formula (XVI)

In the above formulae (XV) and (XVI), Ar is the same as defined in formula (I); X' represents a substituted or unsubstituted monovalent aromatic group, a divalent aromatic group containing one or more substituted or unsubstituted thiophene rings; $R^{11}$ represents a hydrogen atom, an alkyl group, a substituted or unsubstituted aryl group or a substituted or unsubstituted aralkyl group; G' represents a bromine atom or a chlorine atom; and n indicates an integer of from 0 to 5.

The aforementioned homo-coupling reaction is conducted in a solvent by combining the compound of formula (XVI) with a nickel complex, triphenyiphosphine and zinc. When the halogen atom to be introduced is a chlorine atom, the halogen atom (chlorine atom) may have been introduced in advance before a triarylamine skeleton is formed through a coupling reaction using a copper catalyst.

Examples of the nickel complex used in this reaction include nickel chloride, nickel bromide and nickel acetate. The nickel complex is used in an amount of preferably 0.001 to 3 equivalents, and more preferably 0.1 to 2 equivalents, based on 1 equivalent of the compound of formula (XVI).

Also, it is preferable to cause the reaction in the co-existence of a reducing agent such as zinc. The amount of the reducing agent used is preferably 0.001 to 3 equivalents, and more preferably 0.1 to 2 equivalents, based on 1 equivalent of the compound of formula (XVI).

Moreover, triphenylphosphine is used in an amount of preferably 0.5 to 3 equivalents, and more preferably 0.7 to 2 equivalents, based on 1 equivalent of the compound of formula (XVI). As the solvent used for the reaction, dimethylformamide (DMF), dimethylacetamide (DMA), tetrahydrofuran (THF), dimethoxyethane (DME), N-methylpyrrolidone (NMP) and the like may be used. The solvent is used in an amount of preferably 0.1 to 10 equivalents, and more preferably 2 to 5 equivalents, relative to the compound of formula (XVI).

Also, this reaction may be conducted at a temperature ranging from 0 to 100° C., and preferably from ambient temperature to 50° C., with providing sufficient stirring in an atmosphere of inert gas such as nitrogen or argon. After the reaction is completed, the reaction solution is poured into water, followed by vigorous stirring. When the reaction product is in the form of crystals, a crude product may be obtained through suction filtration. When the reaction product is an oily product, it may be extracted with a proper solvent such as ethyl acetate or toluene to obtain a crude product. The crude product thus obtained is column-purified, for example, by using silica gel, alumina, activated clay or activated carbon or by adding these adsorbents to the solution so as to adsorb unnecessary substances. Further, if the reaction product is in the form of crystals, the crystals are re-crystallized, for purification, from a proper solvent such as hexane, methanol, acetone, ethanol, ethyl acetate or toluene.

Hereinafter, the thiophene-containing compound polymer according to the invention will be explained.

The thiophene-containing compound polymer according to the invention is represented by the following formula (V-1) or (V-2).

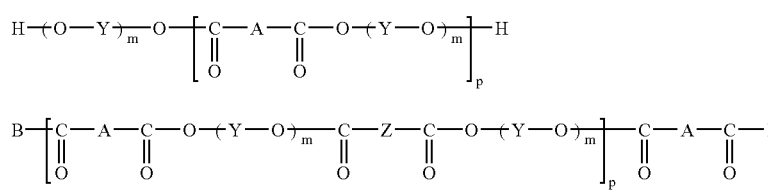

Formula (V-1)

Formula (V-2)

In the above formulae (V-1) and (V-2), Y represents a divalent hydrocarbon group. Z represents a divalent hydrocarbon group. B and B' each represent $-O-(Y-O)_m-H$ or $-O-(Y-O)_m-CO-Z-CO-OR^2$, in which $R^2$ represents a hydrogen atom, an alkyl group, a substituted or unsubstituted aryl group, or a substituted or unsubstituted aralkyl group. m indicates an integer of from 1 to 5. p indicates an integer of from 5 to 5,000. A represents a group represented by the following formula (VI).

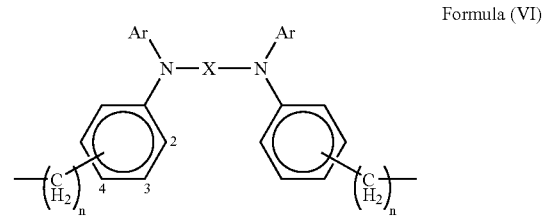

Formula (VI)

Ar, X and n in the above formula (VI) each independently have the same meaning as Ar, X and n defined in the foregoing formula (I), and preferable examples of Ar and X are the same as those of Ar and X defined in formula (I). Two of Ar and two of n, present in formula (VI), may be represent different groups and different integers, respectively.

Also, Y and Z in the above formulae (V-1) and (V-2) are respectively preferably a group represented by any one selected from the group consisting of the following formulae (VII-1) to (VII-7).

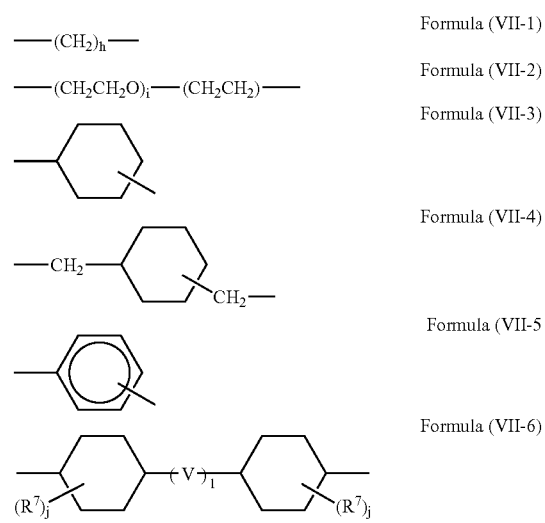

-continued

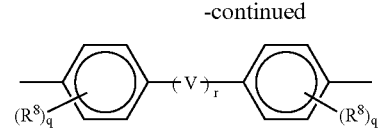

Formula (VII-7)

In formulae (VII-1) to (VII-7), $R^7$ and $R^8$ each independently represent a hydrogen atom, an alkyl group having 1 to 4 carbon atoms, an alkoxy group having 1 to 4 carbon atoms, a substituted or unsubstituted phenyl group, a substituted or unsubstituted aralkyl group or a halogen atom; h and i each indicate an integer of from 1 to 10; j and q each indicate 0, 1 or 2; l and r each indicate 0 or 1; and V represents a group of formulae (III-1) to (III-11).

The degree of polymerization (p in the above formulae (V-1) and (V-2)) of the thiophene-containing compound polymer of the invention is 5 to 5,000. The degree of polymerization is preferably in a range from 10 to 1,000 in view of film-forming ability and stability of the element. Also, a weight average molecular weight Mw is preferably in the range of 10,000 to 300,000.

Specific examples (Exemplary Compounds 101 to 171) of the thiophene-containing compound polymer represented by formula (V-1) or (V-2) according to the invention will be shown below: however, these examples are not intended to be limiting of the invention. Among the thiophene-containing compound polymers, those in which X is a group represented by any one of the following formulae (VIII-1) to (VIII-4) (polymers having a biphenyl structure or terphenyl structure) exhibit high mobility, quantum efficiency and high practicability, and therefore are particularly preferable. In the following Tables 5 to 13, the bonding position indicates a position at which —$(CH_2)_n$— is bound (meaning that, in the formula shown above each table, —$(CH_2)_n$— is bound at one of the positions on the benzene ring having either the numbers of 2 to 4 or 2' to 4'). Also, each of Y, m, p, Ar and n which are all present in a plural number indicates a group or an integer shown in the table. Further, each of Y, m and Z shown in columns B and B' indicates a group or an integer shown in the table.

TABLE 5

| Polymer No. | X | Ar | Bonding Position | n | Y | m | p |
|---|---|---|---|---|---|---|---|
| 101 | phenyl | thiophene-phenyl | 4,4' | 2 | —$CH_2CH_2$— | 1 | 101 |
| 102 | methylphenyl | thiophene-phenyl | 3,3' | 2 | —$CH_2CH_2$— | 1 | 98 |
| 103 | phenyl | bithiophene-phenyl | 4,4' | 2 | —$CH_2CH_2$— | 1 | 88 |
| 104 | methylphenyl | bithiophene-phenyl | 4,4' | 2 | —$CH_2CH_2$— | 1 | 85 |
| 105 | phenyl | thiophene | 4,4' | 2 | —$CH_2CH_2$— | 1 | 135 |
| 108 | phenyl | phenyl-thiophene-phenyl | 4,4' | 2 | —$CH_2CH_2$— | 1 | 56 |
| 109 | methylphenyl | phenyl-thiophene-phenyl | 3,3' | 2 | cyclohexyl | 1 | 65 |

TABLE 5-continued $$H{+}(O{-}Y)_m{-}O{-}\left[\overset{O}{\underset{\|}{C}}{-}A{-}\overset{O}{\underset{\|}{C}}{-}O{-}(Y{-}O)_m\right]_p H$$

$$A = \left( \begin{array}{c} \text{Ar} \quad \text{Ar} \\ \text{N}{-}\text{X}{-}\text{N} \\ \end{array} \right)$$

| Polymer No. | X | Ar | Bonding Position | n | Y | m | p |
|---|---|---|---|---|---|---|---|
| 111 | phenyl | phenyl-thiophene-phenyl-thiophene-phenyl | 4,4' | 2 | —CH$_2$CH$_2$— | 1 | 103 |
| 112 | phenyl | biphenyl-thiophene-thiophene-phenyl | 4,4' | 2 | —CH$_2$CH$_2$— | 1 | 84 |

TABLE 6

$$H{+}(O{-}Y)_m{-}O{-}\left[\overset{O}{\underset{\|}{C}}{-}A{-}\overset{O}{\underset{\|}{C}}{-}O{-}(Y{-}O)_m\right]_p H$$

$$A = \left( \begin{array}{c} \text{Ar} \quad \text{Ar} \\ \text{N}{-}\text{X}{-}\text{N} \\ \end{array} \right)$$

| Polymer No. | X | Ar | Bonding Position | n | Y | m | p |
|---|---|---|---|---|---|---|---|
| 113 | phenyl | phenyl-thiophene-thiophene-thiophene-phenyl | 4,4' | 2 | —CH$_2$CH$_2$— | 1 | 77 |
| 114 | phenyl | phenyl-thiophene | 4,4' | 2 | —CH$_2$CH$_2$— | 1 | 108 |
| 115 | phenyl | phenyl-thiophene-thiophene | 4,4' | 2 | —CH$_2$CH$_2$— | 1 | 99 |
| 116 | biphenyl | thiophene-phenyl | 4,4' | 2 | —CH$_2$CH$_2$— | 1 | 34 |
| 117 | biphenyl | thiophene-thiophene-phenyl | 4,4' | 2 | —CH$_2$CH$_2$— | 1 | 46 |
| 119 | biphenyl | thiophene-thiophene | 4,4' | 2 | —CH$_2$CH$_2$— | 1 | 97 |

TABLE 6-continued

| Polymer No. | X | Ar | Bonding Position | n | Y | m | p |
|---|---|---|---|---|---|---|---|
| 120 | biphenyl | terthiophene | 4,4' | 2 | cyclohexyl | 1 | 163 |
| 121 | biphenyl | phenyl-thiophene-phenyl | 4,4' | 3 | —CH$_2$CH$_2$— | 1 | 101 |
| 123 | biphenyl | phenyl-thiophene-phenyl-thiophene-phenyl | 4,4' | 3 | dimethylcyclohexyl | 1 | 98 |

TABLE 7

| Polymer No. | X | Ar | Bonding Position | n | Y | m | p |
|---|---|---|---|---|---|---|---|
| 124 | biphenyl | phenyl-thiophene-thiophene-phenyl | 4,4' | 2 | —CH$_2$CH$_2$— | 1 | 106 |
| 125 | biphenyl | phenyl-terthiophene-phenyl | 4,4' | 2 | —CH$_2$CH$_2$— | 1 | 163 |
| 126 | biphenyl | phenyl-thiophene | 4,4' | 2 | —CH$_2$CH$_2$— | 1 | 125 |
| 127 | biphenyl | phenyl-bithiophene | 4,4' | 3 | —CH$_2$CH$_2$— | 1 | 100 |
| 128 | dimethylbiphenyl | thiophene-phenyl | 4,4' | 2 | —CH$_2$CH$_2$— | 1 | 95 |

TABLE 7-continued $$H-(O-Y)_m-O-\left[\overset{\overset{O}{\|}}{C}-A-\overset{\overset{O}{\|}}{C}-O-(Y-O)_m\right]_p-H$$

$$A = \left( \begin{array}{c} \text{Ar} \quad \text{Ar} \\ | \quad | \\ N-X-N \\ \text{(phenyl)}_2{-}_3 \quad {}_{3'}{-}_{2'}\text{(phenyl)} \\ (CH_2)_n{-}_4 \quad {}_{4'}{-}(CH_2)_n \end{array} \right)$$

| Polymer No. | X | Ar | Bonding Position | n | Y | m | p |
|---|---|---|---|---|---|---|---|
| 131 | 3,3'-dimethyl-4,4'-biphenylene | thien-2-yl | 4,4' | 2 | —CH$_2$CH$_2$— | 1 | 56 |
| 132 | 3,3'-dimethyl-4,4'-biphenylene | 2,2'-bithien-5-yl | 4,4' | 2 | —CH$_2$CH$_2$— | 1 | 70 |
| 133 | 3,3'-dimethyl-4,4'-biphenylene | 2,2':5',2''-terthien-5-yl | 4,4' | 2 | —CH$_2$CH$_2$— | 1 | 199 |
| 135 | 3,3'-dimethyl-4,4'-biphenylene | 5-(4-(5-phenyl-thien-2-yl)phenyl)thien-2-yl | 4,4' | 2 | —CH$_2$CH$_2$— | 1 | 38 |

TABLE 8

$$H-(O-Y)_m-O-\left[\overset{\overset{O}{\|}}{C}-A-\overset{\overset{O}{\|}}{C}-O-(Y-O)_m\right]_p-H$$

$$A = \left( \begin{array}{c} \text{Ar} \quad \text{Ar} \\ | \quad | \\ N-X-N \\ \text{(phenyl)}_2{-}_3 \quad {}_{3'}{-}_{2'}\text{(phenyl)} \\ (CH_2)_n{-}_4 \quad {}_{4'}{-}(CH_2)_n \end{array} \right)$$

| Polymer No. | X | Ar | Bonding Position | n | Y | m | p |
|---|---|---|---|---|---|---|---|
| 136 | 3,3'-dimethyl-4,4'-biphenylene | 5-phenyl-5''-phenyl-2,2':5',2''-terthien-yl (phenyl-thienyl-phenyl-thienyl-phenyl) | 4,4' | 3 | —CH$_2$CH$_2$— | 1 | 40 |
| 138 | 3,3'-dimethyl-4,4'-biphenylene | phenyl-thienyl-thienyl-thienyl-phenyl | 3,3' | 2 | 1,4-cyclohexylene | 1 | 123 |

TABLE 8-continued
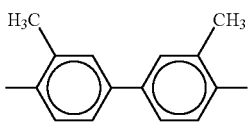
| Polymer No. | X | Ar | Bonding Position | n | Y | m | p |
|---|---|---|---|---|---|---|---|
| 139 | 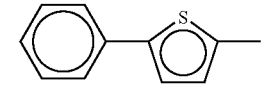 | 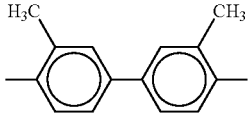 | 4,4' | 2 | —CH$_2$CH$_2$— | 1 | 106 |
| 140 |  | 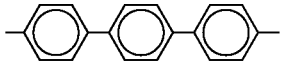 | 4,4' | 3 | —CH$_2$CH$_2$— | 1 | 28 |
| 141 | 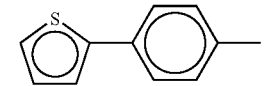 | 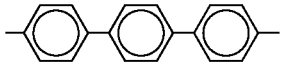 | 4,4' | 2 | —CH$_2$CH$_2$— | 1 | 104 |
| 142 | 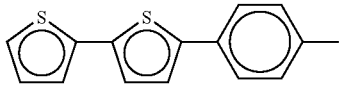 | 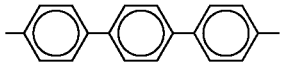 | 4,4' | 2 | —CH$_2$CH$_2$— | 1 | 95 |
| 144 | 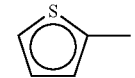 | 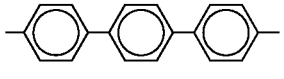 | 4,4' | 2 | —CH$_2$CH$_2$— | 1 | 100 |
| 145 | 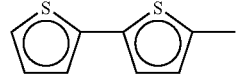 | 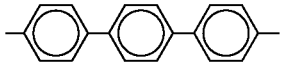 | 4,4' | 2 | —CH$_2$CH$_2$— | 1 | 57 |
| 146 | 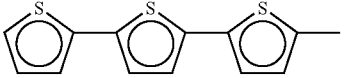 | 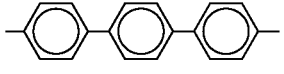 | 4,4' | 2 | —CH$_2$CH$_2$— | 1 | 108 |
TABLE 9
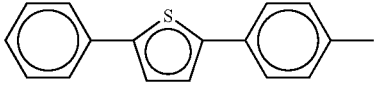
| Polymer No. | X | Ar | Bonding Position | n | Y | m | p |
|---|---|---|---|---|---|---|---|
| 147 | | | 4,4' | 2 | —CH$_2$CH$_2$— | 1 | 67 |

TABLE 9-continued
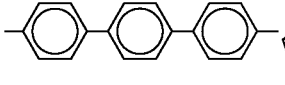
| Polymer No. | X | Ar | Bonding Position | n | Y | m | p |
|---|---|---|---|---|---|---|---|
| 148 | 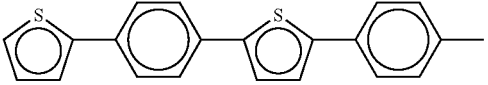 |  | 4,4' | 2 | —CH$_2$CH$_2$— | 1 | 140 |
| 149 | 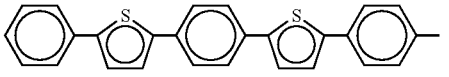 | 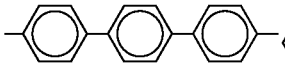 | 4,4' | 3 | —CH$_2$CH$_2$— | 1 | 123 |
| 150 | 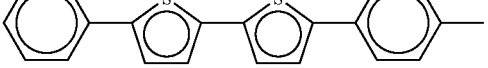 | 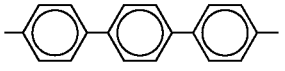 | 4,4' | 2 | —CH$_2$CH$_2$— | 1 | 123 |
| 151 | 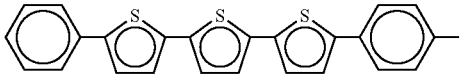 | 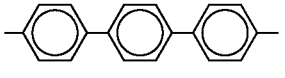 | 3,3' | 2 | —CH$_2$CH$_2$— | 1 | 105 |
| 152 | 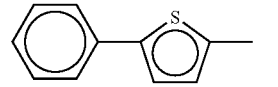 | 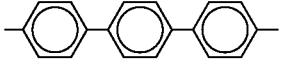 | 3,3' | 2 | —CH$_2$CH$_2$— | 1 | 84 |
| 153 | 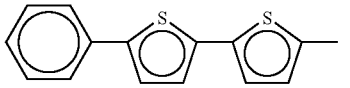 | 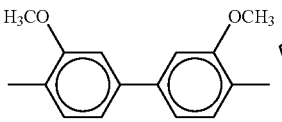 | 4,4' | 3 | —CH$_2$CH$_2$— | 1 | 95 |
| 154 | 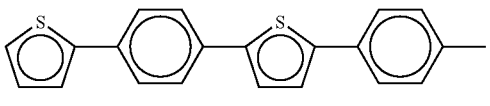 | 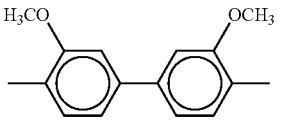 | 4,4' | 2 | —CH$_2$CH$_2$— | 1 | 30 |
| 156 | 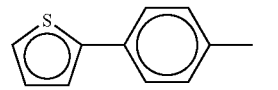 |  | 4,4' | 2 | —CH$_2$CH$_2$— | 1 | 61 |

TABLE 10
| Polymer No. | X | Ar | Bonding Position | n | Y | m | p |
|---|---|---|---|---|---|---|---|
| 158 | 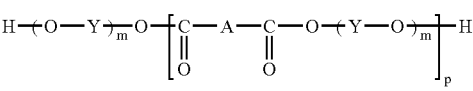 | 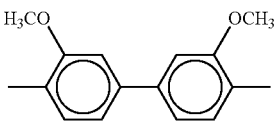 | 4,4' | 2 | —CH₂CH₂— | 1 | 112 |
| 159 | 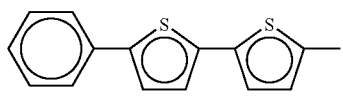 | 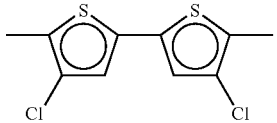 | 4,4' | 2 | —CH₂CH₂— | 1 | 105 |
| 161 | 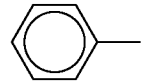 | 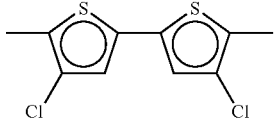 | 4,4' | 2 | 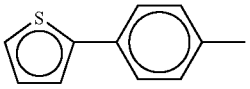 | 1 | 156 |
| 163 | 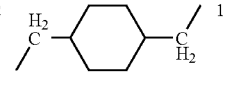 | 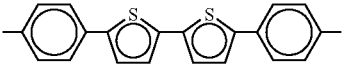 | 4,4' | 2 | —CH₂CH₂— | 1 | 136 |
| 164 | 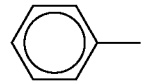 | 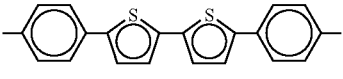 | 4,4' | 2 | —CH₂CH₂— | 1 | 143 |
| 165 | 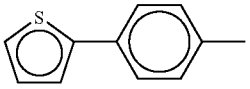 | 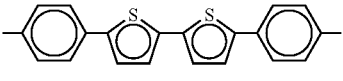 | 4,4' | 2 | 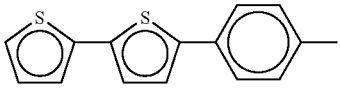 | 1 | 89 |
| 166 | 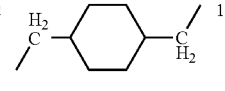 | 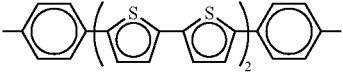 | 4,4' | 2 | —CH₂CH₂— | 1 | 54 |
| 168 | 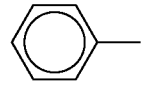 | 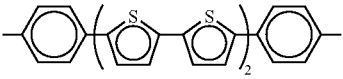 | 4,4' | 2 | 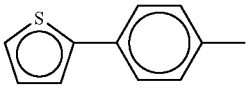 | 1 | 120 |

TABLE 11

| Polymer No. | X | Y | Bonding Position | n |
|---|---|---|---|---|
| 169 | phenyl-(bithiophene)₂-phenyl | bithiophene-phenyl | 4,4' | |
| 170 | bithiophene | biphenyl | 4,4' | 2 |

| Polymer No. | Y | m | p |
|---|---|---|---|
| 169 | CH₂-cyclohexyl-CH₂ | 1 | 101 |
| 170 | —CH₂CH₂— | 1 | 98 |

TABLE 12

| Polymer No. | X | Ar | Bonding Position | n |
|---|---|---|---|---|
| 106 | phenyl | bithiophene | 4,4' | 2 |
| 107 | phenyl | terthiophene | 4,4' | 2 |
| 110 | phenyl | thiophene-phenyl-thiophene-phenyl | 4,4' | 2 |
| 118 | biphenyl | thiophene | 4,4' | 2 |

TABLE 12-continued

| No. | (structure 1) | (structure 2) | | |
|---|---|---|---|---|
| 122 | biphenyl | thiophene-phenyl-thiophene-phenyl | 4,4' | 2 |
| 129 | 3,3'-dimethylbiphenyl | thiophene-phenyl | 4,4' | 2 |
| 130 | 3,3'-dimethylbiphenyl | bithiophene-phenyl | 4,4' | 2 |
| 134 | 3,3'-dimethylbiphenyl | phenyl-thiophene-phenyl | 3,3' | 2 |
| 137 | 3,3'-dimethylbiphenyl | phenyl-bithiophene-phenyl | 4,4' | 2 |
| 143 | terphenyl | bithiophene-phenyl | 4,4' | 2 |

| Polymer No. | B | B' | Y | Z | m | p |
|---|---|---|---|---|---|---|
| 106 | —O—(Y—O)$_m$—H | —O—(Y—O)$_m$—H | —CH$_2$CH$_2$— | p-phenylene | 1 | 98 |
| 107 | —O—(Y—O)$_m$—H | —O—(Y—O)$_m$—H | —CH$_2$CH$_2$— | m-phenylene | 2 | 110 |
| 110 | —O—(Y—O)$_m$—H | —O—(Y—O)$_m$—H | cyclohexylene | —(CH$_2$)$_4$— | 1 | 92 |
| 118 | —O—(Y—O)$_m$—C—Z—C—CH$_3$<br>‖  ‖<br>O  O | —O—(Y—O)$_m$—C—Z—C—CH$_3$<br>‖  ‖<br>O  O | —CH$_2$CH$_2$— | p-phenylene | 1 | 102 |
| 122 | —O—(Y—O)$_m$—H | —O—(Y—O)$_m$—H | cyclohexylene | cyclohexylene | 1 | 100 |
| 129 | —O—(Y—O)$_m$—H | —O—(Y—O)$_m$—H | —CH$_2$CH$_2$— | —(CH$_2$)$_4$— | 1 | 89 |
| 130 | —O—(Y—O)$_m$—H | —O—(Y—O)$_m$—H | —CH$_2$-cyclohexyl-CH$_2$— | biphenyl | 1 | 84 |
| 134 | —O—(Y—O)$_m$—H | —O—(Y—O)$_m$—H | —CH$_2$CH$_2$— | p-phenylene | 1 | 82 |

TABLE 12-continued
| | | | | | | |
|---|---|---|---|---|---|---|
| 137 | —O—(Y—O)ₘ—H | —O—(Y—O)ₘ—H | —CH₂CH₂— |  | 1 | 105 |
| 143 | —O—(Y—O)ₘ—H | —O—(Y—O)ₘ—H | 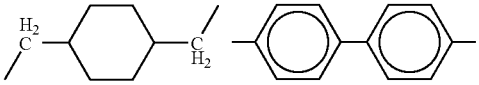 |  | 1 | 88 |
TABLE 13
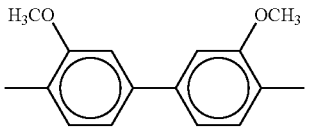
$$A = \left( \begin{array}{c} \text{structure with } N-X-N, Ar, \text{ and } (CH_2)_n \end{array} \right)$$
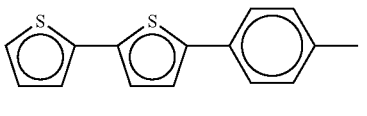
| Polymer No. | X | Ar | Bonding Position | n |
|---|---|---|---|---|
| 157 |  | 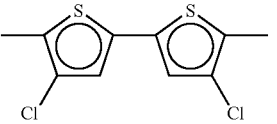 | 4,4' | 2 |
| 160 | 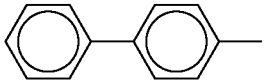 |  | 4,4' | 2 |
| 162 | 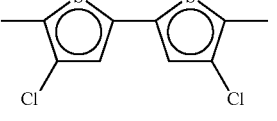 | 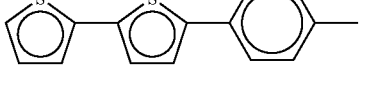 | 4,4' | 2 |
| 167 |  | 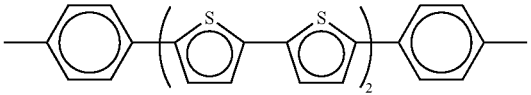 | 4,4' | 2 |
| 171 |  |  | 4,4' | 2 |
| Polymer No. | B | B' | Y | Z | m | p |
|---|---|---|---|---|---|---|
| 157 | 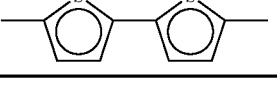 |  | —CH₂CH₂— |  | 1 | 136 |
| 160 | —O—(Y—O)ₘ—H | —O—(Y—O)ₘ—H | —CH₂CH₂— | 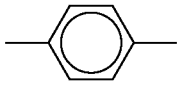 | 1 | 98 |

TABLE 13-continued

| 162 | —O—(Y—O)ₘ—H | —O—(Y—O)ₘ—H | —CH₂CH₂— | ⬡-⬡ | 1 | 56 |
| 167 | —O—(Y—O)ₘ—H | —O—(Y—O)ₘ—H | —CH₂CH₂— | ⬡ | 1 | 164 |
| 171 | —O—(Y—O)ₘ—C(=O)—Z—C(=O)—CH₃ | —O—(Y—O)ₘ—C(=O)—Z—C(=O)—CH₃ | —CH₂CH₂— | ⬡ | 1 | 63 |

The thiophene-containing compound polymer according to the invention may be synthesized by polymerizing the compound of the following formula (XVII), through a known method described in, for example, The 4th edition, Empirical Science Lecture, Vol 28.

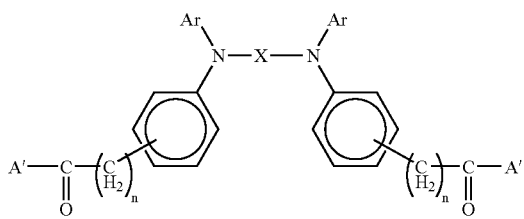

Formula (XVII)

In formula (XVII), Ar, X and n are the same as Ar, X and n defined in the foregoing formula (I). A' represents a hydroxyl group, a halogen atom or a group —O—$R^{12}$, in which $R^{12}$ represents an alkyl group, a substituted or unsubstituted aryl group or aralkyl group.

The thiophene-containing compound polymer of the invention may be synthesized in the following manner.

<1> In Case where A' is a Hydroxyl Group

In case where A' is a hydroxyl group, dihydric alcohols represented by HO—(Y—O)$_m$—H are admixed in almost equal amounts, and polymerization is caused using an acid catalyst. As the acid catalyst, catalysts which are employed in a usual esterifying reaction, such as sulfuric acid, toluenesulfonic acid, trifluoroacetic acid or the like may be used. The acid catalyst is used in an amount ranging from 1/10,000 to 1/10 parts by mass, and preferably 1/1,000 to 1/50 parts by mass, based on 1 part by mass of the monomer. In order to remove water generated in the synthesis, it is preferable to employ a solvent capable of forming an azeotrope with water. As the solvent, toluene, chlorobenzene, 1-chloronaphthalene and the like are effective, and the solvent is used in an amount ranging from 1 to 100 parts by mass, and preferably 2 to 50 parts by mass, based on 1 part by mass of the monomer. Although the reaction temperature is arbitrarily selected, it is preferable to cause a reaction at a boiling temperature of the solvent so as to remove water generated during polymerization. After the reaction is completed, the reaction product is dissolved in a dissolving solvent when no solvent has been used, or when a solvent is used, the reaction solution is, as it is, added dropwise to a poor solvent, such as alcohols, e.g., methanol and ethanol or acetone, in which polymers are scarcely soluble, to thereby precipitate polymers, which are then separated and washed thoroughly with water and organic solvent, followed by drying. Further, if necessary, a re-precipitating process in which the polymer is dissolved in a proper organic solvent, then added dropwise to a poor solvent to precipitate a polymer may be repeated. When the re-precipitating process is carried out, it is preferably carried out with stirring efficiently using a mechanical stirrer or the like. The solvent used to dissolve the polymer in the re-precipitating process is used in an amount ranging from 1 to 100 parts by mass, and preferably 2 to 50 parts by mass, based on 1 part by mass of the polymer. Also, the poor solvent is used in an amount ranging from 1 to 1,000 parts by mass, and preferably from 10 to 500 parts by mass, based on 1 part by mass of the polymer.

<2> In Case where A' is a Halogen

In case where A' is a halogen, dihydric alcohols represented by HO—(Y—O)$_m$—H are admixed in almost equal amounts, and polymerization is effected using an organic basic catalyst such as pyridine or triethylamine. The organic basic catalyst is used in an amount ranging from 1 to 10 equivalents, and preferably from 2 to 5 equivalents, based on 1 part by mass of the monomer. As the solvent, methylene chloride, tetrahydrofuran (THF), toluene, chlorobenzene or 1-chloronaphthalene is effective, and the solvent is used in an amount ranging from 1 to 100 parts by mass, and preferably 2 to 50 parts by mass, based on 1 part by mass of the monomer. The reaction temperature may be arbitrarily selected. After polymerization, the aforementioned re-precipitating process is carried out for purification. Also, in the case of using highly acidic dihydric alcohols such as bisphenols, an interfacial polymerization method may be used. In more detail, water is added to dihydric alcohols, and an equivalent amount of the base is added to dissolve the alcohols. Then, a monomer solution is added in an amount equivalent to that of the dihydric alcohols, with vigorously stirring to thereby cause polymerization. In this case, water is used in an amount ranging from 1 to 1,000 parts by mass, and preferably from 2 to 500 parts by mass, based on 1 part by mass of the divalent alcohols. As the solvent capable of dissolving the monomer, methylene chloride, dichloroethane, trichloroethane, toluene, chlorobenzene and 1-chloronaphthalene are effective. The reaction temperature may be arbitrarily selected, and it is effective to use a phase transfer catalyst such as an ammonium salt or sulfonium salt to facilitate the reaction. The phase transfer catalyst is used in an amount ranging from 0.1 to 10 parts by mass, and preferably from 0.2 to 5 parts by mass, based on 1 part by mass of the monomer.

<3> In Case where A' is —O—R$^{12}$

In case where A' is —O—R$^{12}$, excessive amounts of dihydric alcohols represented by HO—(Y—O)$_m$—H are added and an ester exchange is triggered with heating using an inorganic acid such as sulfuric acid or phosphoric acid, and titanium alkoxide or an acetate or carbonate of calcium, cobalt or the like or an oxide of zinc as the catalyst, and as a result, the thiophene-containing compound polymer can be synthesized. The dihydric alcohols are used in an amount ranging from 2 to 100 equivalents, and preferably from 3 to 50 equivalents, based on 1 equivalent of the monomer. The catalyst is used in an amount ranging from 1/1,000 to 1 part by mass, and preferably from 1/100 to 1/2 parts by mass, based on 1 part by mass of the monomer. It is preferable that the reaction is effected at a reaction temperature of 200 to 300° C., and after the ester exchange from a group —O—R$^{12}$ to a group HO—(Y—O)$_m$—H is completed, the reaction is progressed under reduced pressure to promote the polymerization reaction caused by dissociation of the group HO—(Y—O)$_m$—H Also, it is possible to effect the reaction while removing the group HO—(Y—O)$_m$—H through azeotropic distillation under reduced pressure using a high-boiling solvent such as 1-chloronaphthalene capable of forming an azeotrope with the group HO—(Y—O)$_m$—H.

Furthermore, the thiophene-containing compound polymer of the invention may be synthesized in the following manner. In each of the aforementioned cases, excessive amounts of dihydric alcohols are added to cause the reaction to produce a compound of formula (XVIII). Then, using this compound as a monomer, a reaction may be allowed to cause with, for example, a divalent carboxylic acid or a divalent carboxylic acid halide in the same manner as the above <2>, and as a consequence, a polymer can be obtained.

EXAMPLES

The present invention will now be explained in more detail by way of the following examples.

Example 1

A 500 ml three-neck flask is charged with 25.0 g of acetoanilide, 64.4 g of methyl 4-iodophenylpropionate, 38.3 g of potassium carbonate, 2.3 g of copper sulfate pentahydrate and 50 ml of n-tridecane, and the mixture is stirred under heating at 230° C. for 20 hours in a nitrogen stream. After this reaction, 300 ml of ethylene glycol and 15.6 g of potassium hydroxide are added to the reaction mixture, which is then refluxed under heating for 3.5 hours in a nitrogen stream, then cooled to ambient temperature, poured into 1 l of distilled water and neutralized by hydrochloric acid to thereby precipitate crystals. The crystals are filtered, sufficiently washed with water and then transferred to a 1 L flask. To the crystals is added 500 ml of toluene, followed by refluxing under heating to remove water by azeotropic distillation. Then, 300 ml of methanol and 1.5 ml of concentrated sulfuric acid are added thereto and the resulting mixture is refluxed under heating for 5 hours in a nitrogen stream. After the reaction, the reaction solution is extracted with toluene and the organic phase is sufficiently washed with distilled water. Next, the organic phase is dried by sodium sulfate anhydride, a solvent is evaporated off under reduced pressure and the residue is recrystallized from hexane to obtain 36.5 g of diarylamine. A 200 ml flask is charged with 10.0 g of the thus-obtained diarylamine, 13.4 g of 4-(2-thienyl)-iodobenzene, 8.1 g of potassium carbonate, 0.5 g of copper sulfate pentahydrate and 15 ml of o-dichlorobenzene, and the mixture is refluxed under heating for 10 hours in a nitrogen stream. After the reaction is completed, the reaction mixture is cooled to ambient temperature and dissolved in 100 ml of toluene, and unnecessary

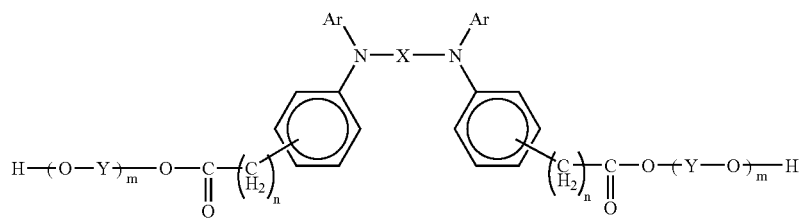

Formula (XVIII)

In the above formula (XVIII), Ar, X and n are the same as Ar, X and n defined in the foregoing formula (I), respectively. Y represents a divalent hydrocarbon group; and m indicates an integer of from 1 to 5.

The thiophene-containing compound and the thiophene-containing compound polymer according to the invention are applicable to organic electronic devices produced from organic materials having charge-transporting properties and luminescent properties. Specifically, the thiophene-containing compound and the thiophene-containing compound polymer according to the invention can be applied to organic electroluminescent elements, electrophotographic photoreceptors, organic thin film transistors, semiconductor lasers and the like.

substances are removed by filtration. An obtained filtrate is purified by silica gel column chromatography using toluene, to thereby give 7.4 g of a thiophene-containing compound (Exemplary Compound 2). A melting point of the resulting thiophene-containing compound is 77 to 79° C. An IR spectrum (obtained using a KBr tablet method) of the thiophene-containing compound is shown in FIG. 1.

Example 2

Figure 2:
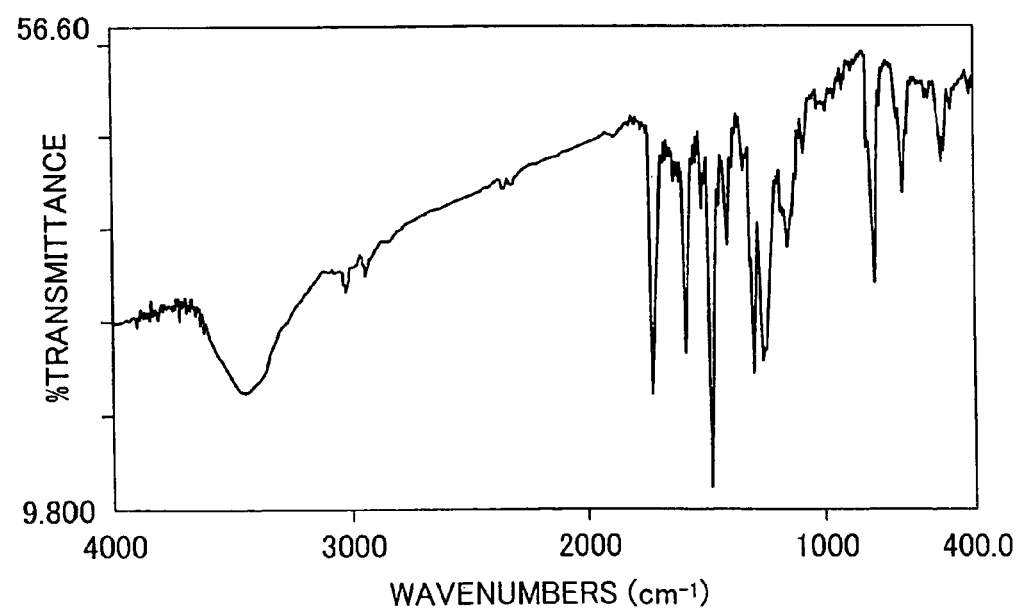
FIG. 2 is an IR spectrum of a thiophene-containing compound (Exemplary Compound 7) obtained in Example 2.
Figure 3:
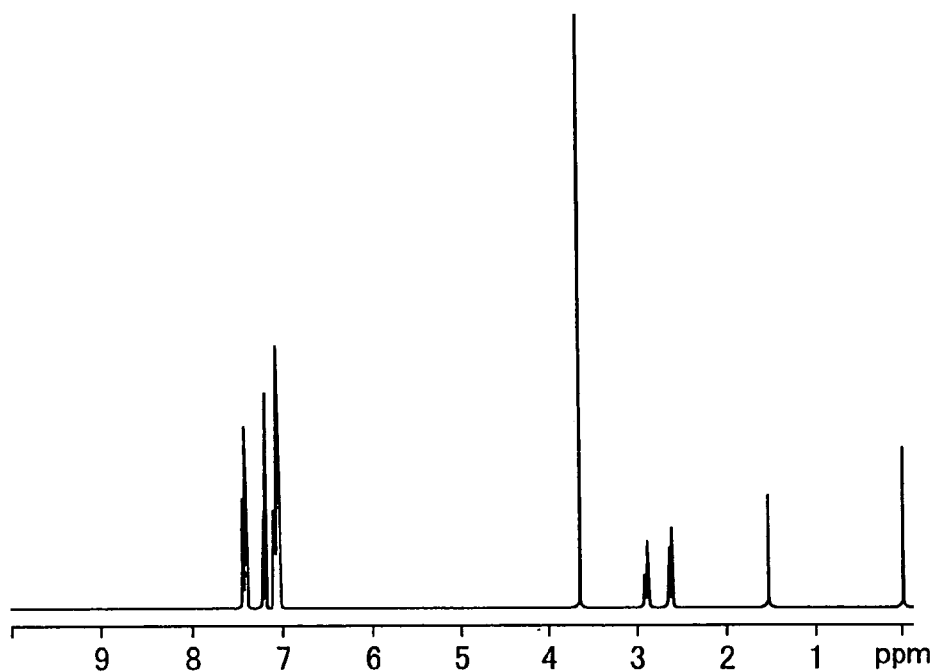
FIG. 3 is a $^1$H-NMR spectrum of a thiophene-containing compound (Exemplary Compound 7) obtained in Example 2.

A 500 ml three-neck flask is charged with 14.0 g of 4-(2-thienyl)acetoanilide, 22.4 g of methyl 4-iodophenylpropionate, 13.4 g of potassium carbonate, 0.8 g of copper sulfate pentahydrate and 40 ml of o-dichlorobenzene, and the mixture is stirred under heating at 200° C. for 15 hours in a nitrogen stream. After this reaction, 100 ml of ethylene glycol and 5.4 g of potassium hydroxide are added to the reaction mixture, which is then refluxed under heating for 3 hours in a nitrogen stream, then cooled to ambient temperature, poured into 300 ml of distilled water and neutralized by hydrochloric acid to thereby precipitate crystals. The crystals are filtered, sufficiently washed with water and then transferred to a 1 L flask. To the crystals is added 500 ml of toluene, followed by refluxing under heating to remove water by azeotropic distillation. Then, 100 ml of methanol and 1 ml of concentrated sulfuric acid are added thereto, and the resulting mixture is refluxed under heating for 2 hours in a nitrogen stream. After the reaction, the reaction solution is dissolved in distilled water and extracted with toluene. The organic phase is sufficiently washed with distilled water. Next, the organic phase is dried by sodium sulfate anhydride, a solvent is evaporated off under reduced pressure and the residue is recrystallized from an ethyl acetate-hexane mixed solution to thereby obtain 15.1 g of diarylamine. A 100 ml flask is charged with 5.5 g of the thus-obtained diarylamine, 3.2 g of 4,4-diiodobiphenyl, 2.2 g of potassium carbonate, 0.2 g of copper sulfate pentahydrate and 10 ml of o-dichlorobenzene, and the mixture is refluxed under heating for 9.5 hours in a nitrogen stream. After the reaction is completed, the reaction mixture is cooled to ambient temperature and dissolved in 100 ml of toluene, and unnecessary substances are removed by filtration. An obtained filtrate is purified by silica gel column chromatography using toluene, to thereby yield 6.2 g of a thiophene-containing compound (Exemplary Compound 7). A melting point of the resulting thiophene-containing compound is 110 to 112° C. The IR spectrum (obtained using a KBr tablet method) of the thiophene-containing compound is shown in FIG. 2. An $^1$H-NMR spectrum (in a $CDCl_3$ solvent) of the thiophene-containing compound is shown in FIG. 3.

Example 3

Figure 4:
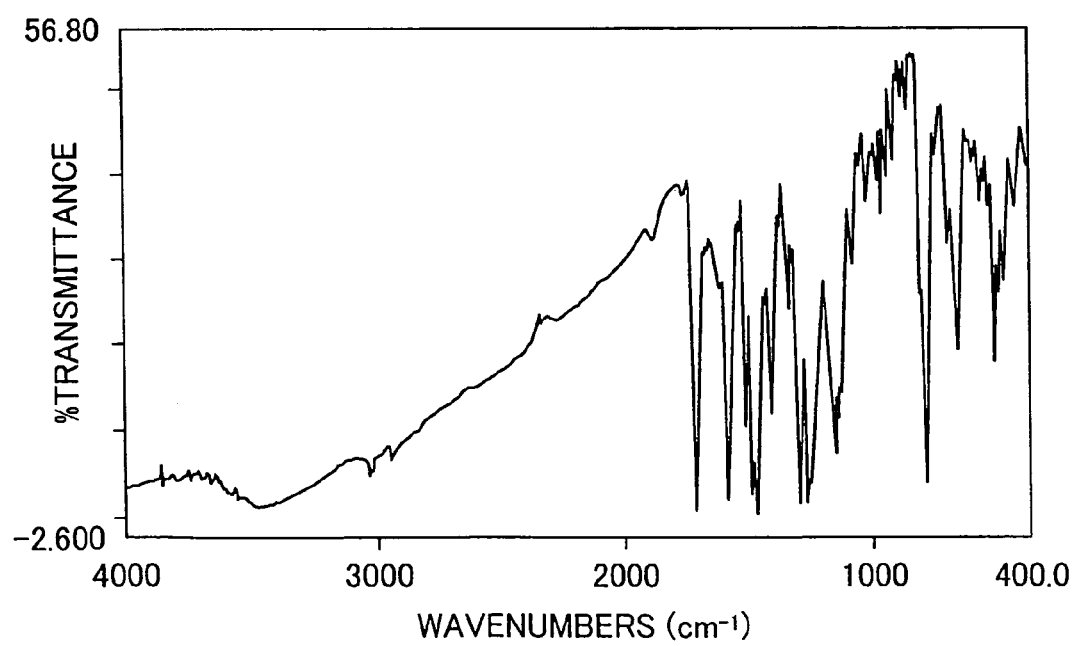
FIG. 4 is an IR spectrum of a thiophene-containing compound (Exemplary Compound 31) obtained in Example 3.
Figure 5:
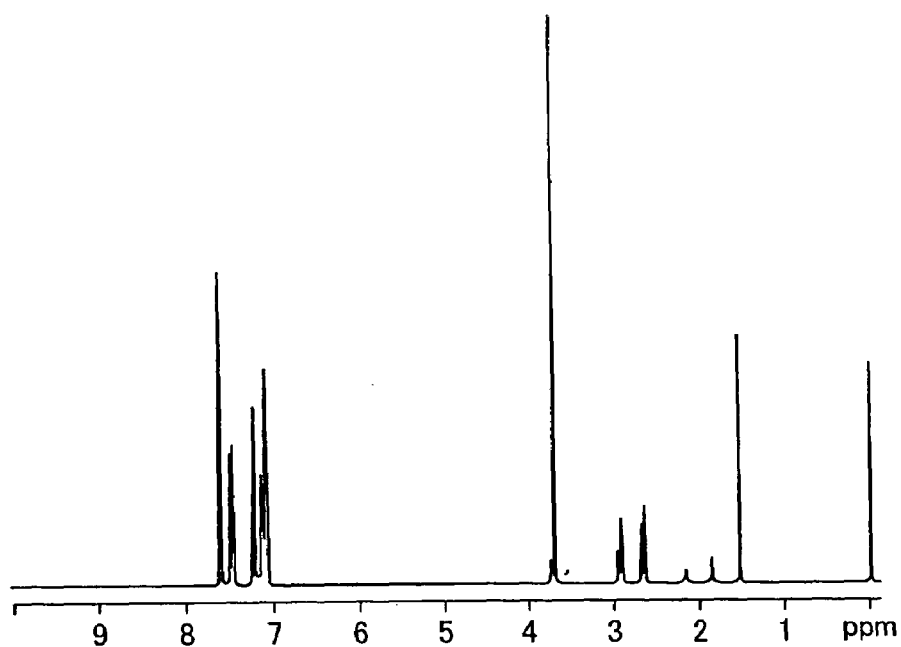
FIG. 5 is a $^1$H-NMR spectrum of a thiophene-containing compound (Exemplary Compound 31) obtained in Example 3.

A 100 ml flask is charged with 5.0 g of diarylamine obtained in the same manner as in Example 2, 3.4 g of 4,4"-diiodo-p-terphenyl, 2.0 g of potassium carbonate, 0.2 g of copper sulfate pentahydrate and 10 ml of o-dichlorobenzene, and the mixture is refluxed under heating at 200° C. for 15 hours in a nitrogen stream. After the reaction is completed, the reaction mixture is cooled to ambient temperature and dissolved in 200 ml of toluene, and unnecessary substances are removed by filtration using celite. An obtained filtrate is purified by silica gel column chromatography using toluene, to thereby afford 4.8 g of a thiophene-containing compound (Exemplary Compound 31). A melting point of the resulting thiophene-containing compound is 230 to 233° C. An IR spectrum (obtained using a KBr tablet method) of the thiophene-containing compound is shown in FIG. 4. An $^1$H-NMR spectrum (in a $CDCl_3$ solvent) of the thiophene-containing compound is shown in FIG. 5.

Example 4

A 300 ml three-neck flask is charged with 20.0 g of 5-(4-iodophenyl)-2,2'-bithiophene, 10.0 g of methyl 4-acetoaminophenylpropionate, 9.4 g of potassium carbonate, 0.6 g of copper sulfate pentahydrate and 20 ml of o-dichlorobenzene, and the mixture is stirred under heating at 200° C. for 13 hours in a nitrogen stream. After this reaction, 75 ml of ethylene glycol and 3.8 g of potassium hydroxide are added to the reaction mixture, which is then refluxed under heating for 3 hours in a nitrogen stream, then cooled to ambient temperature, poured into 150 ml of distilled water and neutralized by hydrochloric acid to thereby precipitate crystals. The crystals are filtered, sufficiently washed with water and then transferred to a 500 ml flask. To the crystals is added 500 ml of toluene, followed by refluxing under heating to remove water by azeotropic distillation. Then, 100 ml of methanol and 1.0 ml of concentrated sulfuric acid are added thereto, and the resulting mixture is refluxed under heating for 5 hours in a nitrogen stream. After the reaction, the reaction solution is extracted with toluene. The organic phase is sufficiently washed with distilled water. Next, the organic phase is dried by sodium sulfate anhydride, a solvent is evaporated off under reduced pressure and the residue is recrystallized from hexane to obtain 13.8 g of diarylamine. A 100 ml flask is charged with 13.0 g of the thus-obtained diarylamine, 5.6 g of 4,4-diiodobiphenyl, 5.0 g of potassium carbonate, 0.5 g of copper sulfate pentahydrate and 40 ml of o-dichlorobenzene, and the mixture is refluxed under heating for 10 hours in a nitrogen stream. After the reaction is completed, the reaction mixture is cooled to ambient temperature and dissolved in 100 ml of toluene, and unnecessary substances are removed by filtration. An obtained filtrate is purified by silica gel column chromatography using toluene, to thereby produce 9.5 g of a thiophene-containing compound (Exemplary Compound 8).

Example 5

A 100 ml flask is charged with 9.9 g of diarylamine obtained in the same manner as in Example 4, 5.4 g of 4,4"-diiodo-p-terphenyl, 3.9 g of potassium carbonate, 0.2 g of copper sulfate pentahydrate and 25 ml of o-dichlorobenzene, and the mixture is stirred under heating at 200° C. for 16 hours in a nitrogen stream. After the reaction is completed, the reaction mixture is cooled to ambient temperature and dissolved in 100 ml of toluene, and unnecessary substances are removed by filtration using celite. An obtained filtrate is purified by silica gel column chromatography using toluene, to thereby give 5.0 g of a thiophene-containing compound (Exemplary Compound 32).

Example 6

10.0 g of the thiophene-containing compound (Exemplary Compound 2) obtained in Example 1 is dissolved in 25 ml of dimethylformamide (DMF), to which is then added 3.4 g of N-chlorosuccinic acid imide (NCS), and the mixture is stirred at ambient temperature for 4 hours in a nitrogen stream. After the reaction is completed, the reaction solution is poured into distilled water to thereby precipitate crystals. The obtained crystals are collected by suction filtration and washed with distilled water to thereby afford 6.4 g of a chloro compound of a thiophene-containing compound (Exemplary Compound 2).

Figure 6:
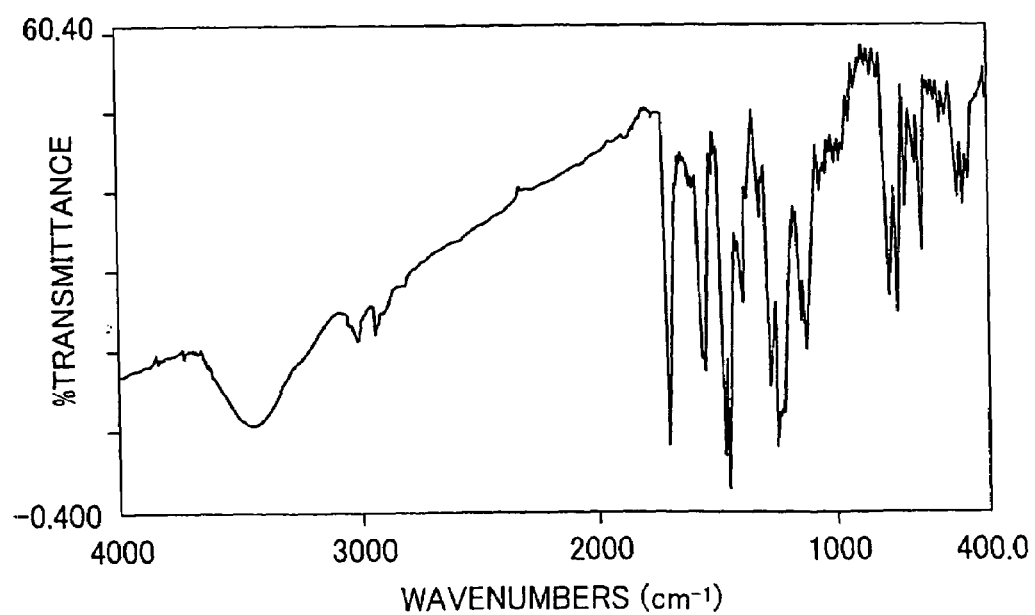
FIG. 6 is an IR spectrum of a thiophene-containing compound (Exemplary Compound 47) obtained in Example 6.
Figure 7:
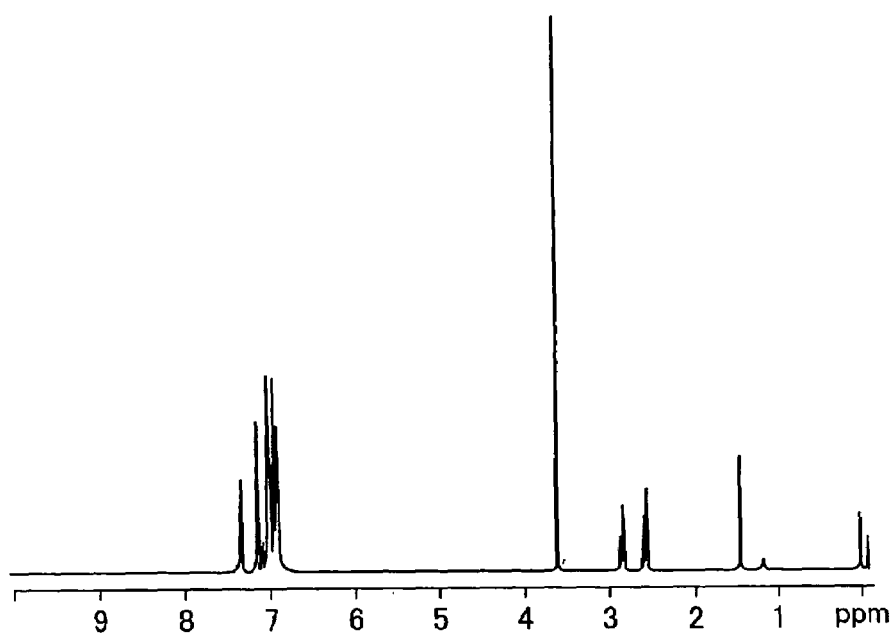
FIG. 7 is a $^1$H-NMR spectrum of a thiophene-containing compound (Exemplary Compound 47) obtained in Example 6.

Next, a 100 ml eggplant-shape flask is charged with 1.7 g of nickel chloride anhydride, 14.0 g of triphenylphosphine and 70 ml of DMF, and the mixture is stirred under heating. When the temperature of the reaction solution is 50° C., 0.9 g of zinc (powder) is added to the reaction mixture, which is then stirred under heating at 50° C. for 1 hour. Thereafter, 6.0 g of the chloro compound "Exemplary Compound 2" is added to the reaction mixture, which is then stirred under heating at 50° C. for 0.5 hours. After the reaction is completed, the reaction solution is cooled to ambient temperature and poured into 500 ml of distilled water, followed by vigorous stirring. The precipitated crystals are collected by suction filtration and washed with distilled water to obtain a crude product. The obtained crude product is purified by silica gel column chromatography using hexane/ethyl acetate. Thus, 10.1 g of a thiophene-containing compound (Exemplary Compound 47) is obtained. A melting point of the obtained thiophene-containing compound is 165 to 167° C. An IR spectrum (obtained using a KBr tablet method) of the thiophene-containing compound is shown in FIG. 6. An $^1$H-NMR spectrum (in a CDCl$_3$ solvent) of the thiophene-containing compound is shown in FIG. 7.

Example 7

A 500 ml three-neck flask is charged with 20.5 g of 4-(2-thienyl)-iodobenzene, 15.0 g of 4-[2-(5-chloro)-thienyl]-acetoanilide, 12.4 g of potassium carbonate, 0.8 g of copper sulfate pentahydrate and 60 ml of o-dichlorobenzene, and the mixture is stirred under heating at 180° C. for 15 hours in a nitrogen stream. After this reaction, 100 ml of ethylene glycol and 5.1 g of potassium hydroxide are added to the reaction mixture, which is then refluxed under heating for 3 hours in a nitrogen stream, then cooled to ambient temperature, poured into 300 ml of distilled water and neutralized by hydrochloric acid to thereby precipitate crystals. The crystals are filtered, sufficiently washed with water and then transferred to a 1 L flask. To the crystals are added 500 ml of toluene, followed by refluxing under heating to remove water by azeotropic distillation. Then, 100 ml of methanol and 1 ml of concentrated sulfuric acid are added and the resulting mixture is refluxed under heating for 2 hours in a nitrogen stream. After the reaction, the reaction solution is dissolved in distilled water and extracted with toluene. The organic phase is sufficiently washed with distilled water. Next, the organic phase is dried by sodium sulfate anhydride, a solvent is evaporated off under reduced pressure and the residue is recrystallized from an ethyl acetate-hexane mixed solution to obtain 14.2 g of diarylamine. A 100 ml flask is charged with 6.0 g of the thus obtained diarylamine, 5.7 g of methyl 4-iodophenylpropionate, 3.4 g of potassium carbonate, 0.2 g of copper sulfate pentahydrate and 15 ml of o-dichlorobenzene, and the mixture is refluxed under heating for 9.5 hours in a nitrogen stream. After the reaction is completed, the reaction mixture is cooled to ambient temperature and dissolved in 100 ml of toluene, and unnecessary substances are removed by filtration. An obtained filtrate is purified by silica gel column chromatography using toluene, to thereby yield 5.6 g of a chloro compound of triarylamine.

Figure 8:
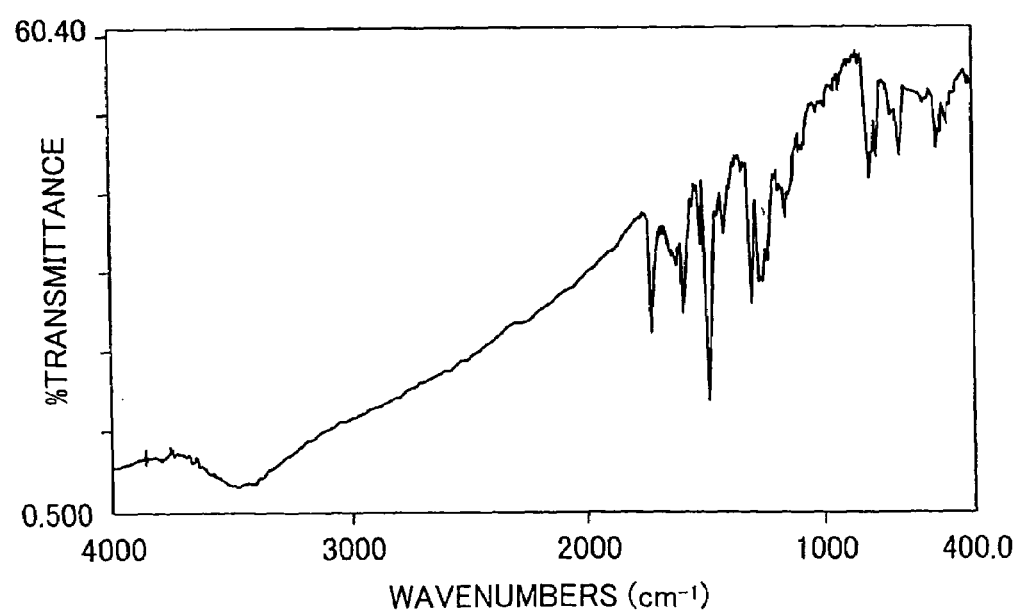
FIG. 8 is an IR spectrum of a thiophene-containing compound (Exemplary Compound 48) obtained in Example 7.
Figure 9:
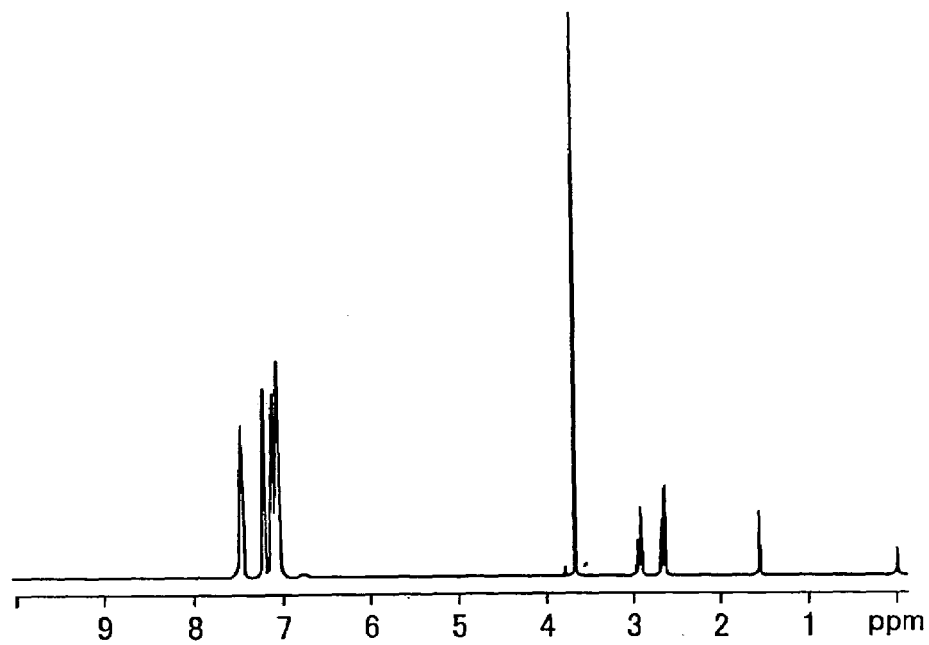
FIG. 9 is a $^1$H-NMR spectrum of a thiophene-containing compound (Exemplary Compound 48) obtained in Example 7.

Next, a 100 ml eggplant-shape flask is charged with 1.3 g of nickel chloride anhydride, 10.5 g of triphenylphosphine and 50 ml of DMF, and the mixture is stirred under heating. When the temperature of the reaction solution is 50° C., 0.7 g of zinc (powder) is added thereto, which is then stirred under heating at 50° C. for 1 hour. Thereafter, 5.3 g of the chloro compound of triarylamine is added to the reaction mixture, which is then stirred under heating at 50° C. for 0.5 hours. After the reaction is completed, the reaction solution is cooled to ambient temperature and poured into 500 ml of distilled water, followed by vigorous stirring. The precipitated crystals are collected by suction filtration and washed with distilled water to obtain a crude product. The obtained crude product is purified by silica gel column chromatography using hexane/ethyl acetate. Thus, 6.4 g of a thiophene-containing compound (Exemplary Compound 48) is obtained. A melting point of the obtained thiophene-containing compound is 103 to 105° C. An IR spectrum (obtained using a KBr tablet method) of the thiophene-containing compound is shown in FIG. 8. An $^1$H-NMR spectrum (in a CDCl$_3$ solvent) of the thiophene-containing compound is shown in FIG. 9.

Example 8

A 200 ml three-neck flask is charged with 10.0 g of diarylamine obtained in the same manner as in Example 1, 9.9 g of 2-iodothiophene, 8.1 g of potassium carbonate, 0.5 g of copper sulfate pentahydrate and 40 ml of o-dichlorobenzene, and the mixture is stirred under heating at 180° C. for 13 hours in a nitrogen stream. After the reaction is completed, the reaction mixture is cooled to ambient temperature and dissolved in 200 ml of toluene, and unnecessary substances are removed by filtration. An obtained filtrate is purified by silica gel column chromatography using toluene, to thereby give 9.8 g of triarylamine. 9.0 g of the resulting triarylamine is dissolved in 30 ml of dimethylformamide (DMF), to which is added 7.1 g of N-chlorosuccinic acid imide (NCS). The mixture is stirred at ambient temperature for 4 hours in a nitrogen stream. After the reaction is completed, the reaction solution is poured into distilled water to precipitate crystals. The obtained crystals are collected by suction filtration and purified by recrystallization to thereby produce 8.6 g of a chloro compound of triarylamine.

Figure 10:
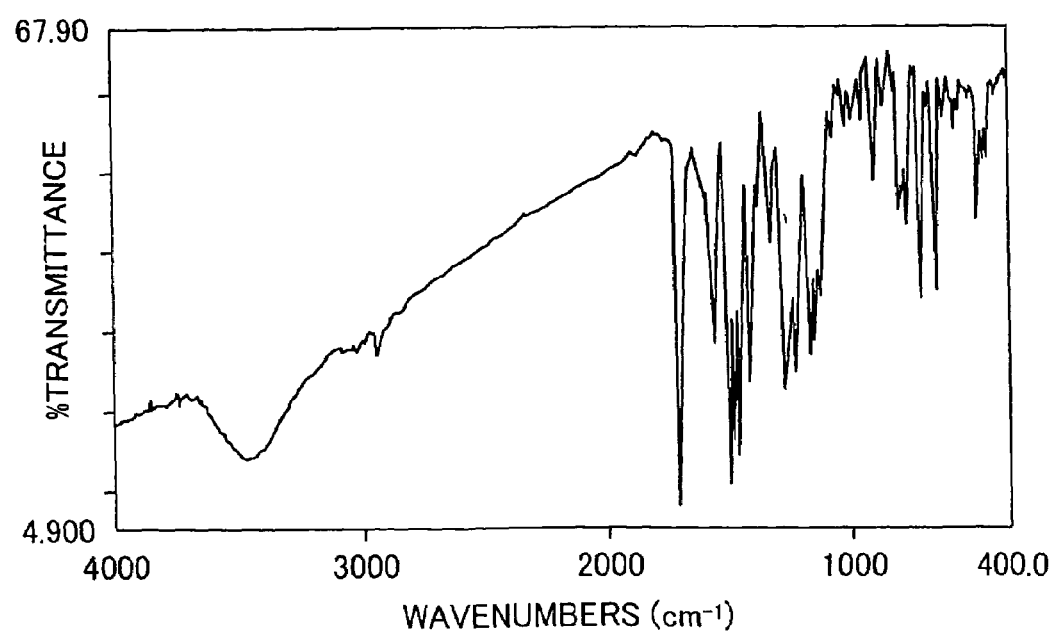
FIG. 10 is an IR spectrum of a thiophene-containing compound (Exemplary Compound 43) obtained in Example 8.
Figure 11:
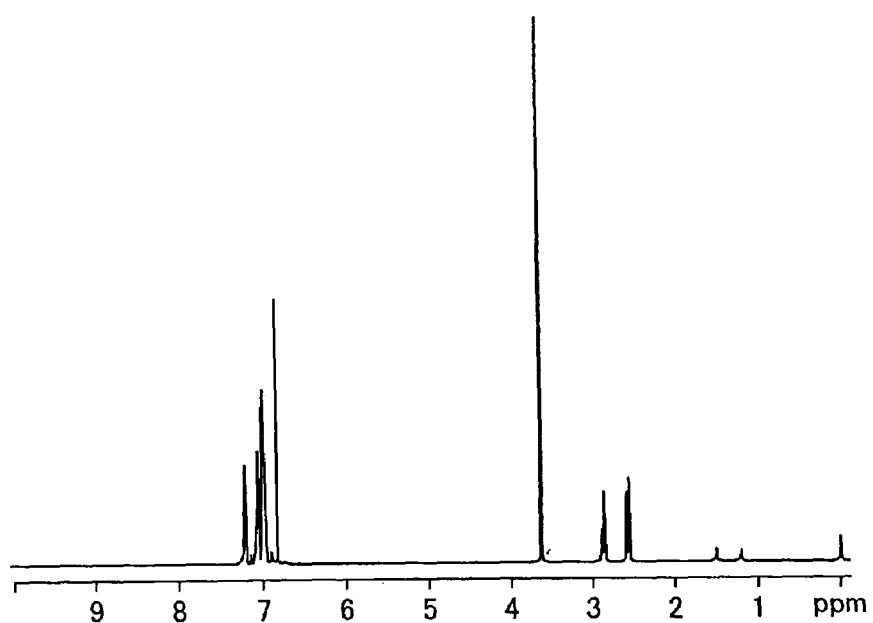
FIG. 11 is a $^1$H-NMR spectrum of a thiophene-containing compound (Exemplary Compound 43) obtained in Example 8.

Next, a 100 ml eggplant-shape flask is charged with 1.3 g of nickel chloride anhydride, 10.5 g of triphenylphosphine and 50 ml of DMF, and the mixture is stirred under heating in a nitrogen stream. When the temperature of the reaction solution is 50° C., 0.7 g of zinc (powder) is added thereto, which is then stirred under heating at 50° C. for 1 hour. Thereafter, 4.1 g of the chloro compound of triarylamine is added to the reaction mixture, which is then stirred under heating at 50° C. for 0.5 hours. After the reaction is completed, the reaction solution is cooled to ambient temperature and poured into 500 ml of distilled water, followed by vigorous stirring to precipitate crystals. The precipitated crystals are collected by suction filtration and washed with distilled water to obtain a crude product. The obtained crude product is purified by silica gel column chromatography using hexane/ethyl acetate, to thereby give 2.7 g of a thiophene-containing compound (Exemplary Compound 43). A melting point of the obtained thiophene-containing compound is 164 to 166° C. An IR spectrum (obtained using a KBr tablet method) of the thiophene-containing compound is shown in FIG. 10. An $^1$H-NMR spectrum (in a CDCl$_3$ solvent) of the thiophene-containing compound is shown in FIG. 11.

Example 9

A 200 ml three-neck flask is charged with 10.0 g of diarylamine obtained in the same manner as in Example 1, 17.3 g of 4-[5-(2,2'-bithienyl)]-iodobenzene, 8.1 g of potassium carbonate, 0.5 g of copper sulfate pentahydrate and 40 ml of o-dichlorobenzene, and the mixture is stirred under heating at 180° C. for 10 hours in a nitrogen stream. After the reaction is completed, the reaction mixture is cooled to ambient temperature and dissolved in 200 ml of toluene, and unnecessary substances are removed by filtration. An obtained filtrate is purified by silica gel column chromatography using toluene, to thereby yield 8.7 g of triarylamine. 5.0 g of the resulting triarylamine is dissolved in 10 ml of dimethylformamide (DMF), to which is added 1.4 g of N-chlorosuccinic acid imide (NCS). The resultant mixture is stirred at ambient temperature for 4 hours in a nitrogen stream. After the reaction is completed, the reaction solution is poured into distilled water to precipitate crystals. The obtained crystals are collected by suction filtration and washed with distilled water to thus obtain 4.6 g of a chloro compound of triarylamine.

Next, a 100 ml eggplant-shape flask is charged with 1.0 g of nickel chloride anhydride, 7.9 g of triphenylphosphine and 40 ml of DMF, and the mixture is stirred under heating in a nitrogen stream. When the temperature of the reaction solution is 50° C., 0.5 g of zinc (powder) is added thereto, which is then stirred under heating at 50° C. for 1 hour. Thereafter, 4.0 g of the chloro compound of triarylamine is added to the reaction mixture, which is then stirred under heating at 50° C. for 0.5 hours. After the reaction is completed, the reaction solution is cooled to ambient temperature and poured into 400 ml of distilled water, followed by vigorous stirring. The precipitated crystals are collected by suction filtration and washed with distilled water to obtain a crude product. The obtained crude product is purified by silica gel column chromatography using hexane/ethyl acetate, to thereby afford 4.7 g of a thiophene-containing compound (Exemplary Compound 50).

Example 10

Figure 12:
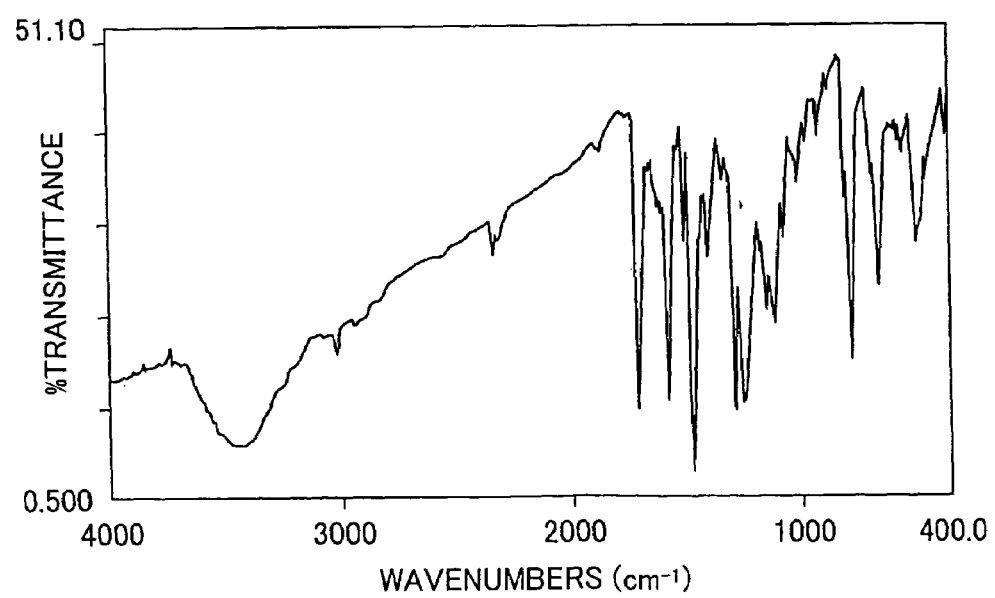
FIG. 12 is an IR spectrum of a thiophene-containing compound polymer (Exemplary Compound 116) obtained in Example 10.
Figure 13:
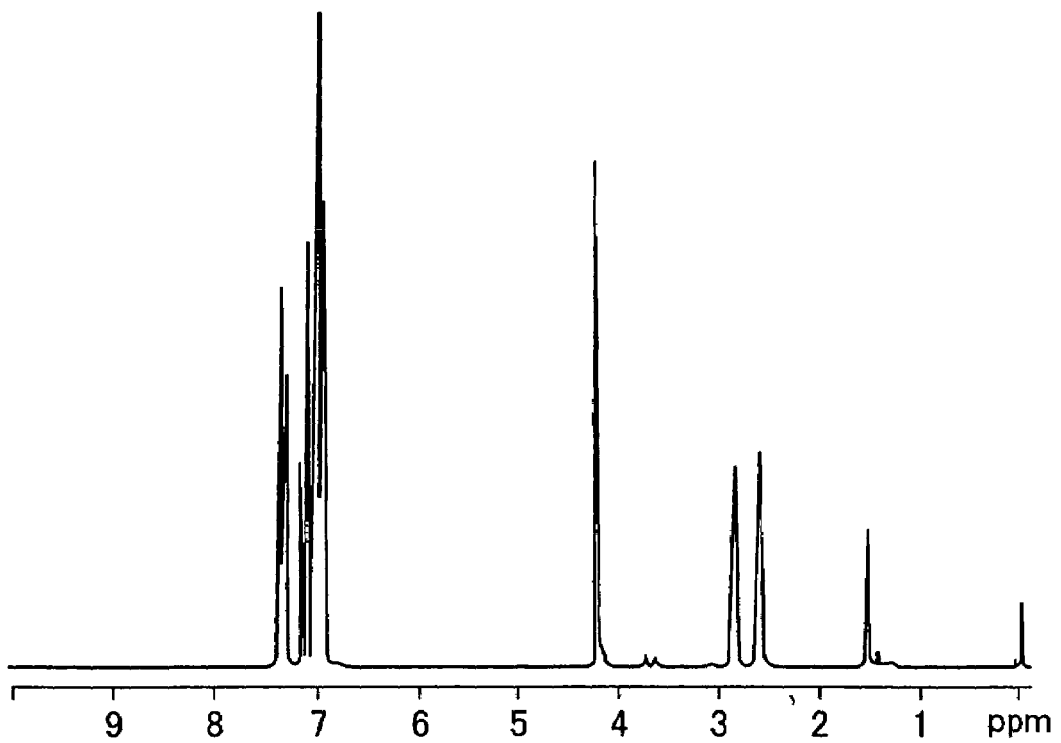
FIG. 13 is a $^1$H-NMR spectrum of a thiophene-containing compound polymer (Exemplary Compound 116) obtained in Example 10.

A 50 ml three-neck flask is charged with 1.0 g of the thiophene-containing compound (Exemplary Compound 7) obtained in Example 2, 10.0 ml of ethylene glycol and 0.02 g of tetrabutoxytitanium, and the mixture is stirred under heating at 200° C. for 7 hours in a nitrogen stream. After it is confirmed that a starting diamine is consumed, a pressure is reduced to 0.5 mmHg to evaporate off ethylene glycol while the mixture is heated to 200° C. to continue the reaction for 4 hours. Thereafter, the reaction solution is cooled to ambient temperature and dissolved in 50 ml of monochlorobenzene. Insoluble substances are removed by filtration using a 0.5 µm polytetrafluoroethylene (PTFE) filter. An obtained filtrate is added dropwise to 600 ml of methanol with stirring to thus precipitate a polymer. The obtained polymer is subjected to filtration and washed thoroughly with methanol, followed by drying to obtain 1.0 g of a thiophene-containing compound polymer (Exemplary Compound 116). A molecular weight of the polymer is measured by GPC, to find that Mw=$2.8\times10^4$ (based on styrene) and p (degree of polymerization) obtained from the molecular weight of the monomer is about 34. An IR spectrum (obtained using a KBr tablet method) of the thiophene-containing compound polymer is shown in FIG. 12. An $^1$H-NMR spectrum (in a $CDCl_3$ solvent) of the thiophene-containing compound polymer is shown in FIG. 13.

Example 11

A 50 ml three-neck flask is charged with 1.0 g of the thiophene-containing compound (Exemplary Compound 31) obtained in Example 3, 7.0 ml of ethylene glycol and 0.04 g of tetrabutoxytitanium, and the mixture is stirred under heating at 200° C. for 5 hours in a nitrogen stream. After it is confirmed that a starting diamine is consumed, a pressure is reduced to 0.5 mmHg to evaporate off ethylene glycol while the mixture is heated to 200° C. to continue the reaction for 4 hours. Thereafter, the reaction solution is cooled to ambient temperature and dissolved in 50 ml of monochlorobenzene. Insoluble substances are removed by filtration using a 0.5 µm polytetrafluoroethylene (PTFE) filter. An obtained filtrate is added dropwise to 600 ml of methanol with stirring to thereby precipitate a polymer. The obtained polymer is subjected to filtration and washed thoroughly with methanol, followed by drying to thus obtain 0.8 g of a thiophene-containing compound polymer (Exemplary Compound 141). A molecular weight of the polymer is measured by GPC, to find that Mw=$9.4\times10^4$ (based on styrene) and p (degree of polymerization) obtained from the molecular weight of the monomer is about 104.

Example 12

A 50 ml three-neck flask is charged with 0.7 g of the thiophene-containing compound (Exemplary Compound 8) obtained in Example 4, 5.0 ml of ethylene glycol and 0.02 g of tetrabutoxytitanium, and the mixture is stirred under heating at 200° C. for 8 hours in a nitrogen stream. After it is confirmed that a starting diamine is consumed, a pressure is reduced to 0.5 mmHg to evaporate off ethylene glycol while the mixture is heated to 200° C. to continue the reaction for 4 hours. Thereafter, the reaction solution is cooled to ambient temperature and dissolved in 40 ml of monochlorobenzene. Insoluble substances are removed by filtration using a 0.5 µm polytetrafluoroethylene (PTFE) filter. An obtained filtrate is added dropwise to 500 ml of methanol with stirring to thereby precipitate a polymer. The obtained polymer is subjected to filtration and washed thoroughly with methanol, followed by drying to thus obtain 0.7 g of a thiophene-containing compound polymer (Exemplary Compound 117). A molecular weight of the polymer is measured by GPC, to find that Mw=$4.6\times10^4$ (based on styrene) and p (degree of polymerization) obtained from the molecular weight of the monomer is about 46.

Example 13

A 50 ml three-neck flask is charged with 0.8 g of the thiophene-containing compound (Exemplary Compound 47) obtained in Example 6, 4.0 ml of ethylene glycol and 0.02 g of tetrabutoxytitanium, and the mixture is stirred under heating at 200° C. for 5 hours in a nitrogen stream. After it is confirmed that a starting diamine is consumed, a pressure is reduced to 0.5 mmHg to evaporate off ethylene glycol while the mixture is heated to 230° C. to continue the reaction for 4 hours. Thereafter, the reaction solution is cooled to ambient temperature and dissolved in 40 ml of monochlorobenzene. Insoluble substances are removed by filtration using a 0.5 µm polytetrafluoroethylene (PTFE) filter. An obtained filtrate is added dropwise to 500 ml of methanol with stirring to thereby precipitate a polymer. The obtained polymer is subjected to filtration and washed thoroughly with methanol, followed by drying to obtain 0.6 g of a thiophene-containing compound polymer (Exemplary Compound 163). A molecular weight of the polymer is measured by GPC, to find that Mw=$1.1\times10^5$ (based on styrene) and p (degree of polymerization) obtained from the molecular weight of the monomer is about 126.

Example 14

A 50 ml three-neck flask is charged with 0.8 g of the thiophene-containing compound (Exemplary Compound 48) obtained in Example 7, 4.0 ml of ethylene glycol and 0.02 g of tetrabutoxytitanium, and the mixture is stirred under heating at 200° C. for 5 hours in a nitrogen stream. After it is confirmed that a starting diamine is consumed, a pressure is reduced to 0.5 mmHg to evaporate off ethylene glycol while the mixture is heated to 230° C. to continue the reaction for 4 hours. Thereafter, the reaction solution is cooled to ambient temperature and dissolved in 40 ml of monochlorobenzene. Insoluble substances are removed by filtration using a 0.5 μm polytetrafluoroethylene (PTFE) filter. An obtained filtrate is added dropwise to 500 ml of methanol with stirring to thereby precipitate a polymer. The obtained polymer is subjected to filtration and washed thoroughly with methanol, followed by drying to obtain 0.6 g of a thiophene-containing compound polymer (Exemplary Compound 164). A molecular weight of the polymer is measured by GPC, to find that Mw=1.4×10$^5$ (based on styrene) and p (degree of polymerization) obtained from the molecular weight of the monomer is about 143.

Example 15

A 50 ml three-neck flask is charged with 2.0 g of the thiophene-containing compound (Exemplary Compound 50) obtained in Example 9, 10.0 ml of ethylene glycol and 0.06 g of tetrabutoxytitanium, and the mixture is stirred under heating at 200° C. for 6 hours in a nitrogen stream. After it is confirmed that a starting diamine is consumed, a pressure is reduced to 0.5 mmHg to evaporate off ethylene glycol while the mixture is heated to 230° C. to continue the reaction for 4 hours. Thereafter, the reaction solution is cooled to ambient temperature and dissolved in 100 ml of monochlorobenzene. Insoluble substances are removed by filtration using a 0.5 μm polytetrafluoroethylene (PTFE) filter. An obtained filtrate is added dropwise to 1 L of methanol with stirring to thereby precipitate a polymer. The obtained polymer is subjected to filtration and washed thoroughly with methanol, followed by drying to thus obtain 1.9 g of a thiophene-containing compound polymer (Exemplary Compound 166). A molecular weight of the polymer is measured by GPC, to find that Mw=5.4×10$^4$ (based on styrene) and p (degree of polymerization) obtained from the molecular weight of the monomer is about 54.

Comparative Example 1

In order to compare it with the thiophene-containing compounds and the thiophene-containing compound polymer according to the present invention obtained in the above examples, MEH-PPV ((Poly[2-methoxy-5-(2'-ethylhexoxy)-1,4-phenylenevinylene] (weight average molecular weight=86,000)) is prepared and subjected to the following evaluation.

(Evaluation)

The thiophene-containing compounds obtained in Examples 1, 2, 6 and 7, the thiophene-containing compound polymer obtained in Example 10 and MEH-PPV are evaluated for mobility through a Time of Flight method by measuring a glass transition temperature using differential scanning calorimetry (DSC) (Tg/DTA 6200, manufactured by Seiko Instruments Inc.). Further, an absorption spectrum is obtained for the above-described respective products using a Ultraviolet-Visible Absorption Measuring Device (U-4000, manufactured by Hitachi, Ltd.), and an emission spectrum is also obtained using a He—Cd laser (excitation wavelength: 325 nm) (PMA-11, manufactured by Hamamatsu Photonics K.K.). The results are shown in Table 14 below.

TABLE 14

| | Mobility (cm$^2$/Vs) | Absorption Wavelength (nm λmax) | Light Emission Wavelength (nm λmax) | Glass Transition Temperature (° C.) |
|---|---|---|---|---|
| Example 1 | 2 × 10$^{-6}$ | 344 | 423 | 6 |
| Example 2 | 4 × 10$^{-6}$ | 365 | 425 | 72 |
| Example 6 | 2 × 10$^{-6}$ | 414 | 491 | 48 |
| Example 7 | 5 × 10$^{-6}$ | 418 | 500 | 77 |
| Example 10 | 1 × 10$^{-4}$ | 367 | 424 | 141 |
| Comparative Example 1 | 1 × 10$^{-8}$ to 1 × 10$^{-7}$ | 479 | 550 | 75 |

As seen from the results shown in Table 14, it is revealed that both of the thiophene-containing compound and the thiophene-containing compound polymer according to the invention have high mobility as well as good luminous properties.

As detailed above, the present invention can provide a novel thiophene-containing compound and a novel thiophene-containing compound polymer which have a high charge-transporting property, are excellent in both solubility and film-forming ability, can be easily synthesized and also exhibit good luminous properties.

What is claimed is:

1. A thiophene-containing compound represented by the following formula (I):

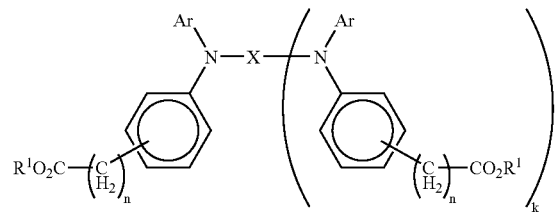

Formula (I)

wherein, in formula (I), Ar represents one or more thiophene rings, a monovalent aromatic group containing one or more thiophene rings or a monovalent aromatic group; X represents one or more thiophene rings, a monovalent or divalent aromatic group containing one or more thiophene rings or a monovalent or divalent aromatic group, in which all of the thiophene rings and aromatic groups may be unsubstituted or further may have a substituent; R$^1$ represents a hydrogen atom, an alkyl group, a substituted or unsubstituted aryl group or a substituted or unsubstituted aralkyl group; n indicates an integer of from 0 to 5; and k indicates 0 or 1; provided that at least one of Ar and X contains a thiophene ring.

2. The thiophene-containing compound according to claim 1, wherein X in formula (I) represents a group represented by any one selected from the group consisting of the following formulae (II-1) to (II-4):

Formula (II-1)

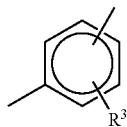

Formula (II-2)

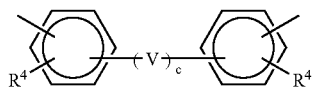

Formula (II-3)

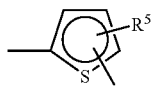

Formula (II-4)

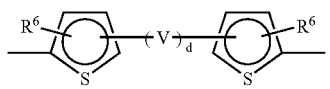

wherein, in formulae (II-1) to (II-4), $R^3$, $R^4$, $R^5$ and $R^6$ each independently represent a hydrogen atom, an alkyl group, an alkoxy group, a substituted or unsubstituted aryl group, a substituted or unsubstituted aralkyl group or a halogen atom; c and d each indicate an integer of from 0 to 5; and V represents a group represented by any one selected from the group consisting of the following formulae (III-1) to (III-11):

Formula (III-1)

—(CH$_2$)$_e$—

Formula (III-2)

—C(CH$_3$)$_2$—

Formula (III-3)

—O—

Formula (III-4)

—S—

Formula (III-5)

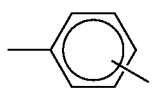

Formula (III-6)

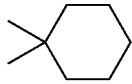

Formula (III-7)

—C(CF$_3$)$_2$—

Formula (III-8)

—Si(CH$_3$)$_2$—

Formula (III-9)

—CH═CH—

Formula (III-10)

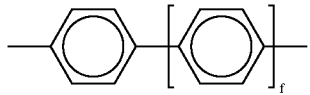

Formula (III-11)

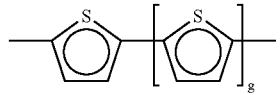

wherein, in formulae (III-1) to (III-11), e indicates an integer of from 1 to 5; and f and g each indicate an integer of from 0 to 5.

3. The thiophene-containing compound according to claim 1, wherein X in formula (I) represents a group represented by any one selected from the group consisting of the following formulae (IV-1) to (IV-4):

Formula (IV-1)

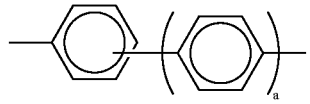

Formula (IV-2)

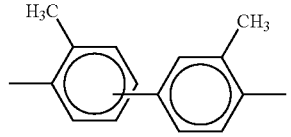

Formula (IV-3)

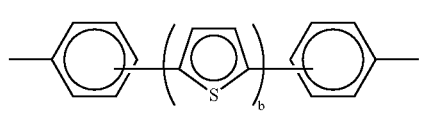

Formula (IV-4)

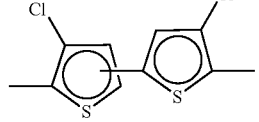

wherein, in formulae (II-1) to (II-4), a indicates an integer of from 0 to 10; and b indicates an integer of from 1 to 10.

4. The thiophene-containing compound according to claim 1, wherein the one or more thiophene rings represented by Ar are selected from the group consisting of a thienyl group, bithienyl group and terthienyl group.

5. The thiophene-containing compound according to claim 1, wherein the monovalent aromatic group represented by Ar is a monovalent aromatic group having 1 to 10 aromatic rings.

6. The thiophene-containing compound according to claim 1, wherein $R^1$ in formula (I) is selected from the group consisting of a hydrogen atom, an alkyl group, a substituted or unsubstituted aryl group and a substituted or unsubstituted aralkyl group.

7. The thiophene-containing compound according to claim 6, wherein the alkyl group represented by $R^1$ is selected from the group consisting of a methyl group, an ethyl group, a propyl group and an isopropyl group.

8. The thiophene-containing compound according to claim 6, wherein the substituted or unsubstituted aryl group represented by $R^1$ is a phenyl group or a tolyl group.

9. The thiophene-containing compound according to claim 6, wherein the substituted or unsubstituted aralkyl group represented by $R^1$ is a benzyl group or a phenethyl group.

10. A thiophene-containing compound polymer represented by the following formula (V-1) or (V-2):

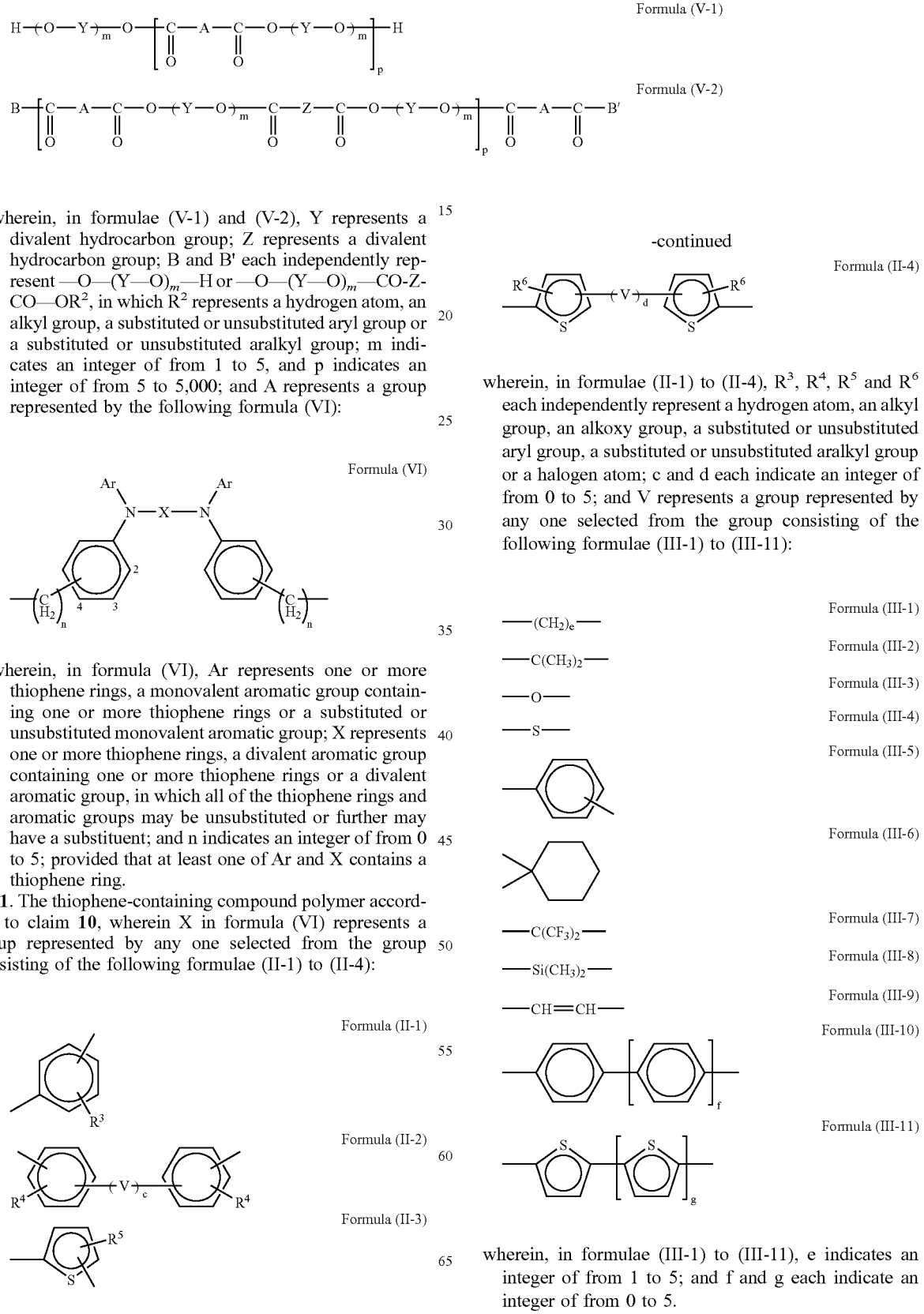

wherein, in formulae (V-1) and (V-2), Y represents a divalent hydrocarbon group; Z represents a divalent hydrocarbon group; B and B' each independently represent —O—(Y—O)$_m$—H or —O—(Y—O)$_m$—CO-Z-CO—OR$^2$, in which R$^2$ represents a hydrogen atom, an alkyl group, a substituted or unsubstituted aryl group or a substituted or unsubstituted aralkyl group; m indicates an integer of from 1 to 5, and p indicates an integer of from 5 to 5,000; and A represents a group represented by the following formula (VI):

Formula (VI)

wherein, in formula (VI), Ar represents one or more thiophene rings, a monovalent aromatic group containing one or more thiophene rings or a substituted or unsubstituted monovalent aromatic group; X represents one or more thiophene rings, a divalent aromatic group containing one or more thiophene rings or a divalent aromatic group, in which all of the thiophene rings and aromatic groups may be unsubstituted or further may have a substituent; and n indicates an integer of from 0 to 5; provided that at least one of Ar and X contains a thiophene ring.

11. The thiophene-containing compound polymer according to claim 10, wherein X in formula (VI) represents a group represented by any one selected from the group consisting of the following formulae (II-1) to (II-4):

Formula (II-1)

Formula (II-2)

Formula (II-3)

Formula (II-4)

wherein, in formulae (II-1) to (II-4), R$^3$, R$^4$, R$^5$ and R$^6$ each independently represent a hydrogen atom, an alkyl group, an alkoxy group, a substituted or unsubstituted aryl group, a substituted or unsubstituted aralkyl group or a halogen atom; c and d each indicate an integer of from 0 to 5; and V represents a group represented by any one selected from the group consisting of the following formulae (III-1) to (III-11):

—(CH$_2$)$_e$—  Formula (III-1)

—C(CH$_3$)$_2$—  Formula (III-2)

—O—  Formula (III-3)

—S—  Formula (III-4)

Formula (III-5)

Formula (III-6)

—C(CF$_3$)$_2$—  Formula (III-7)

—Si(CH$_3$)$_2$—  Formula (III-8)

—CH=CH—  Formula (III-9)

Formula (III-10)

Formula (III-11)

wherein, in formulae (III-1) to (III-11), e indicates an integer of from 1 to 5; and f and g each indicate an integer of from 0 to 5.

12. The thiophene-containing compound polymer according to claim 10, wherein X in formula (VI) represents a group represented by any one selected from the group consisting of the following formulae (IV-1) to (IV-4):

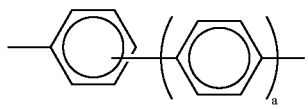

Formula (IV-1)

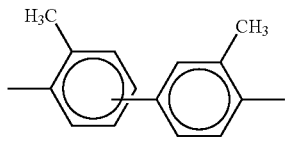

Formula (IV-2)

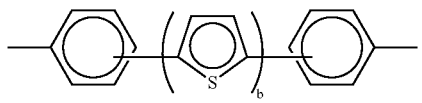

Formula (IV-3)

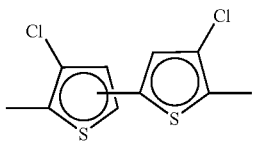

Formula (IV-4)

wherein, in formulae (II-1) to (II-4), a indicates an integer of from 0 to 10; and b indicates an integer of from 1 to 10.

13. The thiophene-containing compound polymer according to claim 10, having a polymerization degree ranging from 5 to 5,000.

14. The thiophene-containing compound polymer according to claim 13, having a polymerization degree ranging from 10 to 1,000.

15. The thiophene-containing compound polymer according to claim 10, having a weight average molecular weight Mw ranging from 10,000 to 300,000.

* * * * *